(12) United States Patent
Duncan et al.

(10) Patent No.: US 10,988,618 B2
(45) Date of Patent: Apr. 27, 2021

(54) SELF-ASSEMBLED NANO-STRUCTURED PARTICLE AND METHODS FOR PREPARING

(71) Applicant: DYSTAR HILTON DAVIS CORP., Charlotte, NC (US)

(72) Inventors: Gregory David Duncan, Wyoming, OH (US); Jun Wang, Cincinnati, OH (US); Everett William Merling, Beachwood, OH (US); Xiaoming Wu, Hebron, KY (US); James S. Brock, Fort Thomas, KY (US); Kevin M. Henry, Lockland, OH (US); Joseph D. Kern, Montgomery, OH (US)

( * ) Notice: Subject to any disclaimer, the term of this patent is extended or adjusted under 35 U.S.C. 154(b) by 0 days.

(21) Appl. No.: 16/601,098

(22) Filed: Oct. 14, 2019

(65) Prior Publication Data

US 2020/0040191 A1 Feb. 6, 2020

Related U.S. Application Data

(60) Continuation-in-part of application No. 15/261,067, filed on Sep. 9, 2016, now Pat. No. 10,442,932, which
(Continued)

(51) Int. Cl.
*C09B 67/00* (2006.01)
*A61K 47/69* (2017.01)
(Continued)

(52) U.S. Cl.
CPC ...... *C09B 67/0066* (2013.01); *A61K 47/6949* (2017.08); *B82Y 5/00* (2013.01);
(Continued)

(58) Field of Classification Search
None
See application file for complete search history.

(56) References Cited

U.S. PATENT DOCUMENTS 4,365,061 A 12/1982 Szejtli et al.
4,990,280 A 2/1991 Thorengaard et al.
(Continued)

FOREIGN PATENT DOCUMENTS

CA 2181495 A1 1/1997
EP 1284127 A1 2/2003
(Continued)

OTHER PUBLICATIONS

Zhao, B., et al., Adhesion and detachment mechanisms of sugar surfaces from the solid (glassy) to liquid (viscous) states, PNAS, Dec. 26, 2006, vol. 3, No. 52, pp. 19624-19629.
(Continued)

*Primary Examiner* — Jeffrey D Washville
(74) *Attorney, Agent, or Firm* — Hudak, Shunk & Farine Co. LPA

(57) ABSTRACT

Novel, nano-structured particles are formed by introducing a selected solid of interest into a structured fluid matrix formed by a dispersion of a small molecule host vessel components, such as a native or modified polysaccharide, cavitand, simple sugar, disaccharide, simple polyol or other similarly structured molecule known to be useful as a host vessel, in an acidic medium or other solvent, whereby the particle size of the introduced solid is reduced and or limited in the structured fluid matrix, by incorporation into or attachment to, the host vessel. The simple, one-batch mixing process results in stabilized colloidal dispersions of the nanoparticles of a variety of solids of varying scope and function and useful in a wide variety of applications, including without limitation ceramic materials, such as hexagonal boron nitride.

12 Claims, 4 Drawing Sheets

Related U.S. Application Data is a division of application No. 14/346,339, filed as application No. PCT/US2012/056597 on Sep. 21, 2012, now Pat. No. 9,458,322.

(60) Provisional application No. 61/538,175, filed on Sep. 23, 2011.

(51) Int. Cl.
| | | |
|---|---|---|
| *B82Y 5/00* | (2011.01) | |
| *C09B 67/22* | (2006.01) | |
| *C09B 67/20* | (2006.01) | |
| *C09B 67/02* | (2006.01) | |
| *C09B 67/46* | (2006.01) | |

(52) U.S. Cl.
CPC ........ *C09B 67/009* (2013.01); *C09B 67/0022* (2013.01); *C09B 67/0023* (2013.01); *C09B 67/0067* (2013.01); *C09B 67/0091* (2013.01); *C09B 67/0097* (2013.01)

(56) References Cited

U.S. PATENT DOCUMENTS

| | | |
|---|---|---|
| 6,048,736 A | 4/2000 | Kosak |
| 6,171,381 B1 | 1/2001 | Yoshimura et al. |
| 6,432,194 B2 | 8/2002 | Johnson et al. |
| 6,881,421 B1 | 4/2005 | da Silveira et al. |
| 7,030,176 B2 | 4/2006 | Nohr et al. |
| 7,307,110 B2 | 12/2007 | Yatake |
| 7,371,456 B2 | 5/2008 | Nohr et al. |
| 7,462,659 B2 | 12/2008 | Rhee et al. |
| 7,741,384 B2 | 6/2010 | Liu |
| 7,829,698 B2 | 11/2010 | Kim et al. |
| 9,458,322 B2 | 10/2016 | Duncan et al. |
| 2002/0134280 A1 | 9/2002 | Naruse |
| 2003/0195274 A1 | 10/2003 | Nakamara et al. |
| 2004/0265237 A1 | 12/2004 | Kim et al. |
| 2005/0084535 A1* | 4/2005 | Coleman .............. A61K 8/0204 424/489 |
| 2008/0044481 A1 | 2/2008 | Harel |
| 2008/0193520 A1 | 8/2008 | Moschwitzer et al. |
| 2010/0173002 A1 | 7/2010 | Yulai et al. |
| 2011/0150954 A1 | 6/2011 | Lapidot et al. |
| 2013/0253015 A1 | 9/2013 | Majhi et al. |

FOREIGN PATENT DOCUMENTS

| | | |
|---|---|---|
| EP | 1995283 A1 | 11/2008 |
| EP | 2277982 A1 | 1/2011 |
| JP | 63 199781 A | 8/1988 |
| JP | 01 146974 A | 6/1989 |
| JP | 11 106694 A | 4/1999 |
| JP | 2000160077 A | 6/2000 |
| JP | 2001271012 A | 10/2001 |
| JP | 2005350586 A | 12/2005 |
| JP | 2006316225 A | 11/2006 |
| KR | 100258640 B1 | 6/2000 |
| WO | 2006108637 A2 | 10/2006 |

OTHER PUBLICATIONS

Padrino, J.C., et al., Stress-induced cavitation for the streaming motion of a viscous liquid past a sphere, J. Fluid Mech., 2007, vol. 578, pp. 381-411.

Dellinger, T.M., et al., BiOCl Nanoparticles Synthesized in Lyotropic Liquid Crystal Nanoreactors, Scripta mater, 2001, vol. 44, Nos. 8/9, pp. 1893-1897.

Ruths, M., et al., Rate-Dependent Adhesion between Polymer and Surfactant Monolayers on Elastic Substrates, Langmuir 1998, vol. 14, No. 7, pp. 1804-1814.

* cited by examiner

SELF-ASSEMBLED NANO-STRUCTURED PARTICLE AND METHODS FOR PREPARING

FIELD OF THE INVENTION

This invention is directed to novel, stable colloidal dispersions of self-assembled nano-structured particles formed and methods for preparing them. This invention is also directed to methods to improve the chroma and shade of colored nanoparticles, surface adhesion of nanoparticles prepared by the method, selectivity of nanoparticles for surfaces to which they adhere, and stability of nanoparticles and colloidal dispersions of nanoparticles prepared by the methods of the invention. This invention is also directed to use of a wide variety of solid materials having varying scope and functions, the particle size of which has been reduced using the inventive methods. Finally, the invention is directed to a number of applications for use of the nanoparticles and colloidal dispersions thereof prepared according to the methods of the invention.

BACKGROUND OF THE INVENTION

Nanostructures or nanoparticles are plentiful in nature and form the basic building blocks for chemical and biological compositions. Nanoparticles may also be created by artificial means, either chemical or mechanical, or both, to take advantage of property improvements associated with their use. Use of nanoparticles allows greater accessibility and availability of many components for certain applications and may reduce the amount of a component necessary to achieve a given result, thus reducing costs attendant with the use of the component. Small particle size is itself a necessary property for colloidal stability and for high performance of particle dispersions in some applications, including jetting.

Small particles, and in particular, nanoparticles, may be prepared either by reducing the size of larger particles or by constraining growth of particles as they are formed, or by a combination of techniques. For example, the size of larger particles may be reduced by any number of mechanical or physical techniques known to those skilled in the art. These techniques include, without limitation, the application of energy through milling, ultrasound or high sheer mixing, such as, but not limited to, a media mill, ball mill, an attritor, a flow jet mixer, an impeller mill, a colloidal mill, or a sand mill. Alternatively, smaller particles may be formed during synthesis by constraining their growth, for example, by formation in a micro-channel reactor. Finally, particle size may be reduced by dissolving larger particles and constraining growth during recrystallization. This may be accomplished, for example, by precipitating the particles from solution in the presence of surfactants, among other methods known in the art.

More recently, it has been reported that nanostructured particles of inorganic minerals have been formed in lyotropic liquid crystals having hydrophilic and hydrophobic domains within the crystal. This method is not used commercially.

The prior art techniques for creating small particles are not without shortcomings. Typically, the most effective commercial techniques to obtain small particles, including nanoparticles, require reduction of the size of larger particles, accomplished by the application of mechanical or physical energy or constraining particle size growth, as discussed above. These approaches require highly specialized equipment and are time consuming, and both the equipment and processes are expensive.

In addition, smaller particle sizes are generally associated with larger surface areas, and nanoparticles are no exception. Due to their larger surface areas, among other things, nanoparticles require stabilization to prevent agglomeration and maintain their dispersibility in suitable media, making them more accessible or available for their ultimate use. Hence, following reduction of particle size, it is typically necessary to stabilize the nanoparticle dispersion through a separate step.

Colloidal dispersions of small particles, including nanoparticles, may be stabilized by several different techniques, including without limitation i) the addition of polymeric or small molecule surfactants that associate non-covalently with the surface of the particle, ii) through covalent attachment of "stabilizing" small molecules, or iii) polymers to the surface of the small particle, or by encapsulation of the small particle with components that will contribute to the stabilization. Encapsulation may be accomplished, for example, by cross-linking polymeric surfactants or polymerizing monomers, which are then adsorbed to the surface of the particle.

Some stabilization examples from the prior art include U.S. Pat. No. 7,741,384, which is directed to a method of homogenizing a dispersion by coating pigment particles with a polymerized monomer. Similarly, U.S. Pat. No. 7,307,110 describes methods for improving dispersibility of a water-based pigment by treating the surface of the pigment particle with a water-dispersibility-imparting group or encapsulating the pigment particle with a water-dispersible polymer. U.S. Pat. No. 6,432,194 describes methods of attaching functional groups to pigment particles to improve various properties rather than relying on adsorption. U.S. Pat. No. 6,171,381 is directed to an aqueous ink composition wherein cyclodextrin is used as a coating agent; dextrins are also used as dye binders in KR 100258640.

Prior art stabilization techniques involving the addition of surfactants, covalent attachment of "stabilizing" small molecules or polymers to the surface of the particle, or encapsulation of the particle, while useful, are not without disadvantages. Surfactants may change the properties of the dispersion in undesirable ways, such as by increasing viscosity or lowering surface tension, and they may also be expensive. Practical commercial techniques to stabilize small particles by covalent attachment of small molecules or polymers and/or by encapsulation tend to require relatively complex, multi-step chemical processes and may use undesirable or dangerous solvents or reagents. There is, therefore, a need for a process for preparing stabilized nanoparticle dispersions that allow for accessibility and availability of the nanoparticle component in the selected application, without compromising the properties of the dispersion and that are simple and cost effective to produce.

Novel self-assembled nanoparticles and unique processes (methods) for preparing them have been discovered, which avoid the shortcomings of the prior art discussed above. The novel self-assembled nanoparticles of the invention are clathrates formed by the addition of a selected guest solid to a structured fluid or matrix, i.e., a semi-solid or viscoelastic gel, comprising a host vessel or molecule dispersed in an acid or other solvent medium. The host vessel may comprise a number of compounds known to one skilled in the art to be useful as host molecules in supra-molecular chemistry. These include: native or modified polysaccharides; cavitands, such as cyclodextrin, cucurbituril and calixerenes; simple sugars, such as the monosaccharides dextrose, fructose or glucose; disaccharides, such as sucrose (a combination of glucose and fructose); simple (linear, branched, or cyclic) polyols, such as ethylene glycol, propylene glycol, glycerin, sorbitol and xylitol; crown ethers, aza crowns, cryptands, cyclophanes, oligo- and poly-peptides, proteins, oligo- and poly-nucleotides, or other similarly structured molecules. The selected guest solid is entrapped or otherwise included within the host vessel to form a clathrate cage or shell having the selected solid (guest) encompassed within. The particle size of the selected solid is thus reduced or growth is limited by the structural constraints of the host molecule.

It has also been discovered that the properties of self-assembled nanostructured particles and colloidal dispersions thereof may be significantly improved as compared to that achieved by prior methods. In particular, it has been found that the inventive method achieves significant improvements in the chroma and shade of colored nanoparticles, the surface adhesion of nanoparticles prepared by the process, and the selectivity of nanoparticles for the surfaces to which they adhere. In other aspects, the inventive methods provide a means for improving the stability of colloidal dispersions of nanoparticles and storage of process intermediates prior to being put in use. The methods described herein may be used with a great number of solids having diverse, broad scope and functions. The nanoparticles and colloidal dispersions resulting therefrom may be used in a variety of applications as further described herein.

Clathrate or host/guest formations are known in the art, although none of the prior art describes the specific clathrates of the present invention, or processes, for reducing particle size of a selected solid to nanoparticle dimensions through the use of a clathrate and/or stabilizing a colloidal dispersion of nanoparticles, which do not require additional particle size reduction or stabilizing steps. For example, U.S. Patent Publ. No. 2004/265237 discloses a small molecule clathrate useful for improving the solubility and release of platinum based anticancer drugs, but the disclosed clathrate is not a nanoparticle-based clathrate. Similarly, U.S. Pat. No. 6,881,421 discloses a nano-polyalkylcyanoacrylate plus an inclusion compound useful for complexing an "active" in its hydrophobic cavity, useful as a drug carrier. U.S. Pat. No. 7,462,659 discloses uniform nanoparticles useful as pore-forming templates on wafers of electronic material, wherein cyclodextrin is combined with silica to form a low dielectric film. U.S. Pat. No. 7,829,698 describes nanoparticles comprising cucurbituril derivatives and pharmaceutical compositions in THF organic solvent for use as a drug delivery system.

With respect to inks and jetting applications in particular, none of the prior art discloses the novel nanoparticle-based aqueous colloidal dispersions of the present invention. JP 2001271012 describes a nanoparticle-based ink formulation prepared by first mechanically reducing the particle size of the pigment and combining the pigment with a number of components including amides, polyhydric alcohols, urea, glycerin, glycols, ethers, buffers, and water. Cyclodextrin or calixarene are added to aid in dispersibility and stability of the formulation in the same manner as surfactants.

By contrast, a notable feature of the methods of the invention is that they do not require or utilize separate steps to reduce the particle size of the selected solids to nanoparticle dimensions prior to addition to the gel. Rather, reduction of the particle size of selected solids to nanoparticle dimensions is accomplished in a one-step mixing/reaction process involving the addition of the selected solid to a gel comprising a host vessel or molecule dispersed in an acid medium or other solvent. Particle size reduction is accomplished by dissolving and reforming the solid in the host vessel, or by synthesizing the solid directly in the host vessel and annealing the interaction. Mechanical particle size reduction might be used prior to combining the selected solid with the gel, but only for particularly large particles or agglomerates to facilitate reduction to nanoparticles using the inventive process. The invention yields stable colloidal dispersions without the use of other steps outside of the reaction. While not required, additional components may be added at various stages of the batch mixing process or later to the colloidal dispersion to stabilize the resulting nanoparticles and colloidal dispersions thereof, change the affinity for nanoparticles to a surface, improve adhesion to a surface and modify the chroma or shade of nanoparticles.

CA2181495 discloses a water-based printing ink comprising an epoxy, an organic or inorganic pigment, a drier, cyclodextrin and water. Cyclodextrin forms an "inclusion compound" with the drier to protect it and to reduce the amount needed in the ink. Unlike the present invention, the cyclodextrin is not used as a host for the pigment, nor is it stated to reduce the particle size of the selected pigment.

U.S. Pat. Nos. 7,371,456 and 7,030,176 disclose new recording inks with improved properties comprising nanoparticles with colloidal inner cores used as a template to bind a series of layers of colors and a complex process for preparing them. The inks include optional "includant" compounds that may inhibit aggregation of the colors or add to the stability of the inks and cyclodextrin is listed as one such compound. Stability is primarily accomplished by charges on pre-formed polymers. Unlike the present invention, the inks require alternating layers of polymers and/or charged polymers to wrap or attach to colorants. The inks are formed in an oil/water system by high sheer emulsification, using organic solvents. In addition, preparation of the inks starts with a charged nano-particle core of either a charged polymer or a charged silica gel particle. Nothing in either of these patents teach the use of includant compounds to reduce particle size or stabilize the formulation.

The invention provides advantages over the foregoing art. The invention achieves novel self-assembled nanoparticles and colloidal dispersions thereof and provides colloidal stabilization in a single batch mixing process that is safe and environmentally friendly. The inventive processes involve the use of simple techniques to prepare nano-structured particles and stable colloids of these particles that may be easily practiced in, and are viable for, commercial manufacturing. The novel processes are also less costly, because they do not require specialized or additional equipment or separate pre-processing steps, specialized handling or additional components.

Nano-structured particles prepared by the inventive processes have many valuable uses, among them are as stable colloidal dispersions useful for application by jetting technology. Stable, colloidal dispersions of organic color pigments have been prepared using this technology. These dispersions have been used to prepare inks with excellent jetting properties, although the invention is not limited to this application.

Other non-limiting uses of the novel, stable colloidal dispersions of the present invention include, but are not limited to, other types of inks and coatings; electronic and optical materials, such as conductors, insulators, semiconductors, and the like, particularly those useful for devices or manufacturing as by jetting; inorganic, organic and ceramic materials for various other applications; biotechnology materials; antibodies; pharmaceuticals; drug carrier/delivery systems; medical diagnostics and treatment materials; bioassay agents; or imaging materials; storage, sorbent and carrier materials; thermoplastic materials; biological materials; structural applications; and nano-fabrication of devices. Other uses will be evident to one skilled in the art.

The novel, stable colloidal dispersions of the invention have comparable particle size and comparable or better stability than those produced by traditional competitive processes and have demonstrated utility in jetting applications.

It is an object of the invention to provide a simple, one batch method for reducing the particle size of a large variety of solids to nanostructured particles.

It is a further object of the invention to provide stabilized colloidal dispersions of nanoparticles from a wide variety of selected solids.

It is yet another object of the invention to provide commercially viable techniques for producing stabilized colloidal dispersions of nanoparticles of a wide variety of selected solids, which are simple, safe, cost effective and environmentally friendly to perform.

Still other objects of the invention will be evident to one skilled in the art based upon the disclosure herein.

SUMMARY OF THE INVENTION

The invention is directed to novel nano-structured particles and stable colloidal dispersions thereof, novel methods to reduce the particle size of a solid to nanoparticle dimensions by formation in a clathrate structure, and novel methods to prepare clathrate-based structured fluids useful for reducing particle size of a solid and producing stable colloidal dispersions of nanoparticles, without the need for conventional stabilization techniques. In contrast to conventional particle size reduction techniques, the inventive techniques allow for reduction in the particle size of the selected solid to nanoparticles and stabilization of a colloidal dispersion of the nanoparticles so formed in a single step—by annealing in a gel comprising native or modified polysaccharides, cavitands, or other similarly structured molecules known to be useful host vessels in a fluid. The viscoelastic or semi-solid gel resulting from the dispersion of the host vessel in an acid or other solvent is a "structured" fluid matrix that acts as a template for reducing the particle size of an added solid or limiting the growth of particles of compounds that are synthesized within the gel. The colloidal dispersions formed are useful in a number of applications, including but not limited to inkjet applications and other applications discussed above.

In one embodiment, the invention is a novel structured fluid matrix comprising host vessels formed from native or modified polysaccharides, cavitands, simple sugars, such as the monosaccharides dextrose, fructose or glucose, a disaccharide, such as sucrose, simple (linear, branched, or cyclic) polyols, such as ethylene glycol, propylene glycol, or glycerin, crown ethers, aza crowns, cryptands, cyclophanes, oligo- and poly-peptides, proteins, oligo- and poly-nucleotides, or other similarly structured molecules, dispersed in an acid or other solvent medium.

In a second embodiment, the invention is a colloidal dispersion of nano-structured particles formed through the addition of selected guest solids to the novel structured fluid matrix.

In a third embodiment, the invention is a process for converting host molecules/vessels including without limitation native or modified polysaccharides, cavitands, simple sugars, such as the monosaccharides dextrose, fructose or glucose, disaccharides, such as sucrose, simple (linear, branched, or cyclic) polyols, such as ethylene glycol, propylene glycol, or glycerin, crown ethers, aza crowns, cryptands, cyclophanes, oligo- and poly-peptides, proteins, oligo- and poly-nucleotides, and other similarly structured molecules into a structured fluid matrix by mixing the host molecule with an acid medium, which is then used to prepare nano-structured particles by adding selected guest solids to the structured fluid matrix to yield self-assembled nanoparticles and colloidal dispersions thereof.

In a fourth embodiment, the invention is a process for creating a stable nanoparticle colloidal dispersion by (i) fusing small, supra-molecular host molecules into a clathrate cage encompassing the entire nanoparticle, e.g., by caramelizing cyclodextrins or other carbohydrates at the surface of the nanoparticle or (ii) further reacting the colloidal dispersion with other compounds such as bases to remove acids or carboxymethylation of nanoparticles with acids.

In another embodiment, the invention is a process for attaching useful moieties to a nanoparticle through the clathrate cage, e.g. through acetal or hydrazone linkages. This may include moieties that stabilize colloidal dispersions, for example by attaching charged groups that increase the zeta potential of the nanoparticles.

In further embodiment, the invention is a process for improving the properties of nanoparticles, such as chroma or shade, or affinity or selectivity for a surface, by reacting colloidal dispersions of nanoparticles with peroxide bond containing compounds or dihydrazides.

In yet a further embodiment, the invention is a distinctive process technology useful to prepare dispersions for jetting and other stable colloidal dispersions of nanoparticles, by initiating cavitation to reduce the size of solid guest particles in a high viscosity structured fluid.

Still other embodiments of the invention are directed to applications for use of the nanoparticles and colloidal dispersions thereof formed from the inventive processes.

The structured fluids of the invention are prepared by mixing components that are easily removed by membrane filtration. These components include, but are not limited to cavitands, modified polysaccharides, native polysaccharides, simple sugars, such as the monosaccharides dextrose, fructose or glucose, disaccharides, such as sucrose, simple polyols, such as ethylene glycol, propylene, glycerin, sorbitol, xylitol and the like, polyphosphoric acids, mixtures of two or more of these components, and combinations of the mixture with aldehydes or polyaldehydes.

DETAILED DESCRIPTION OF THE INVENTION

Figure 1:
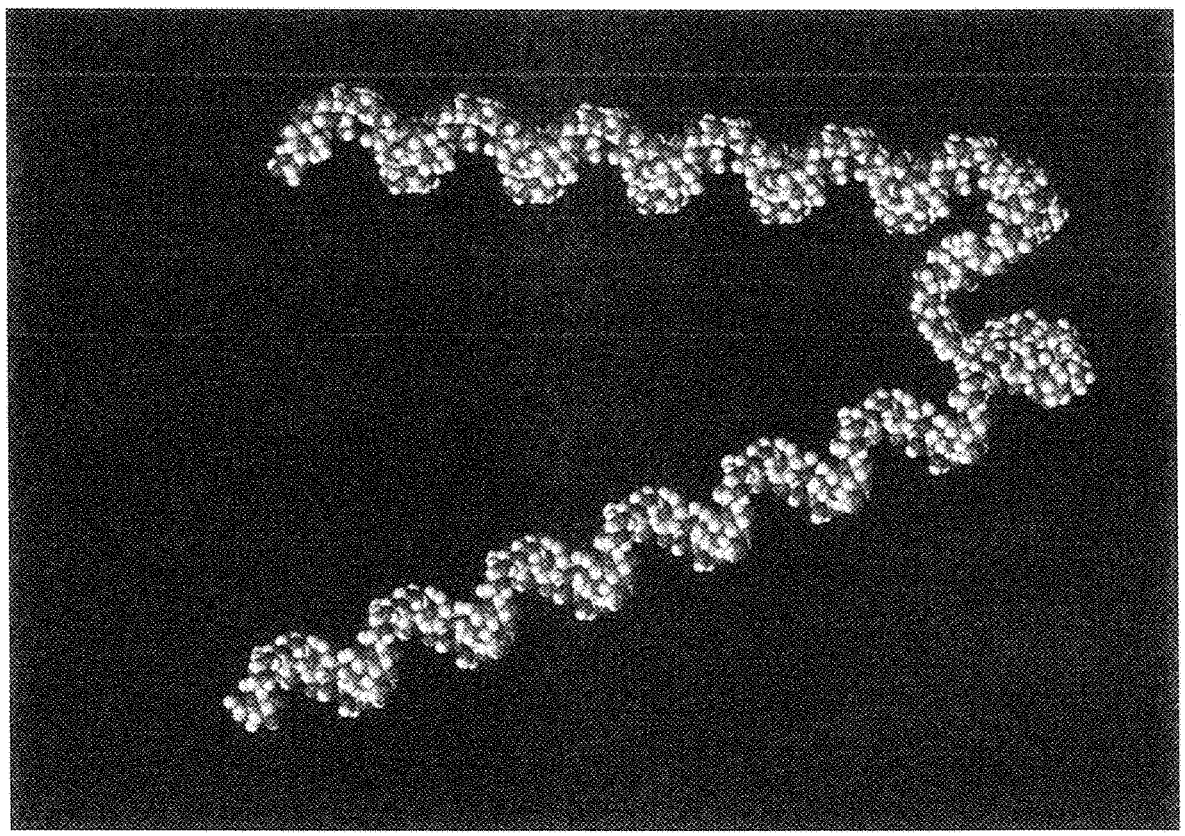
FIG. 1 shows the helical structure of amylose from starch.
Figure 2:
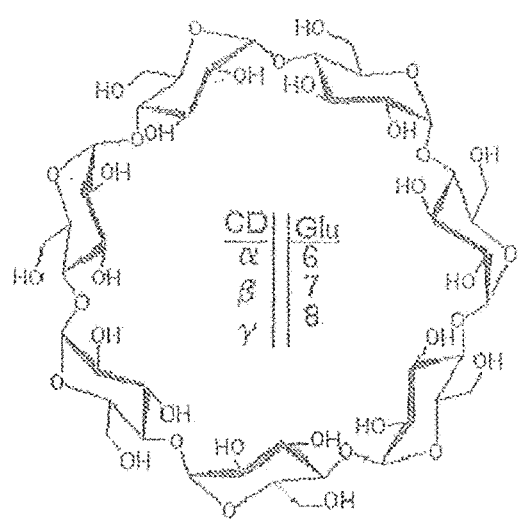
FIG. 2 is a chemical structure of β-cyclodextrin.
Figure 2A:
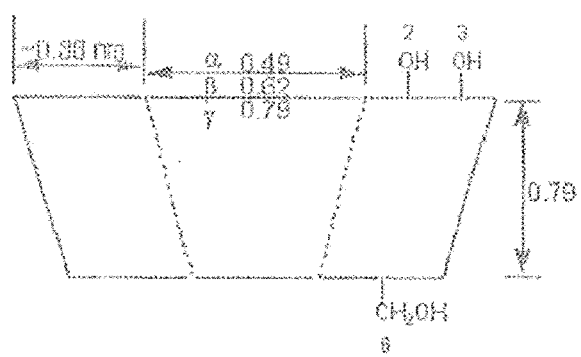
FIG. 2a is a schematic representing structures and dimensions for α, β, and γ-cyclodextrins.
Figure 3:
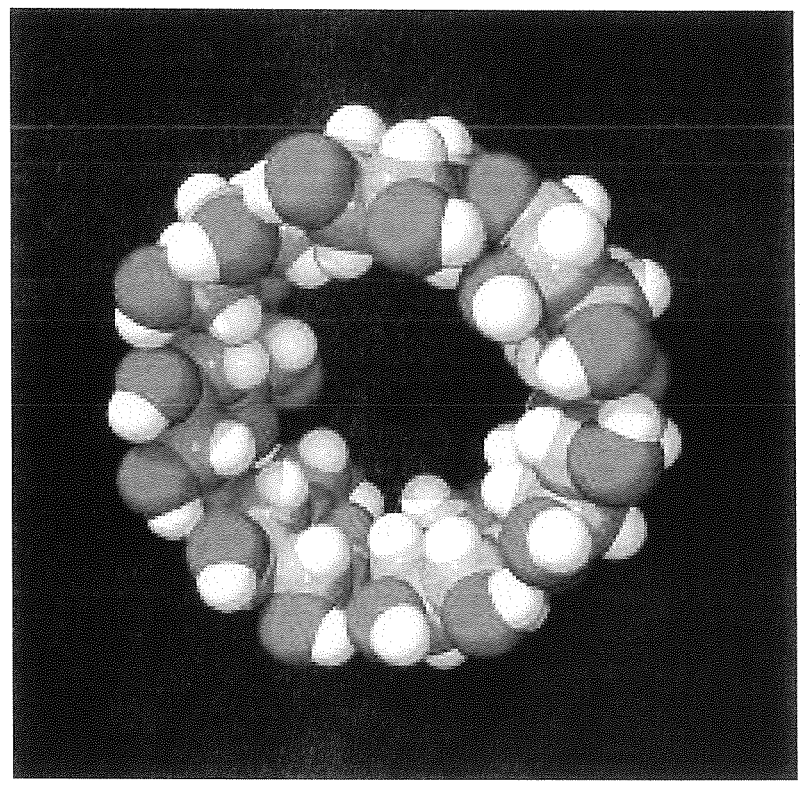
FIG. 3 shows a computer-generated space filled model of β-cyclodextrin.
Figure 4:
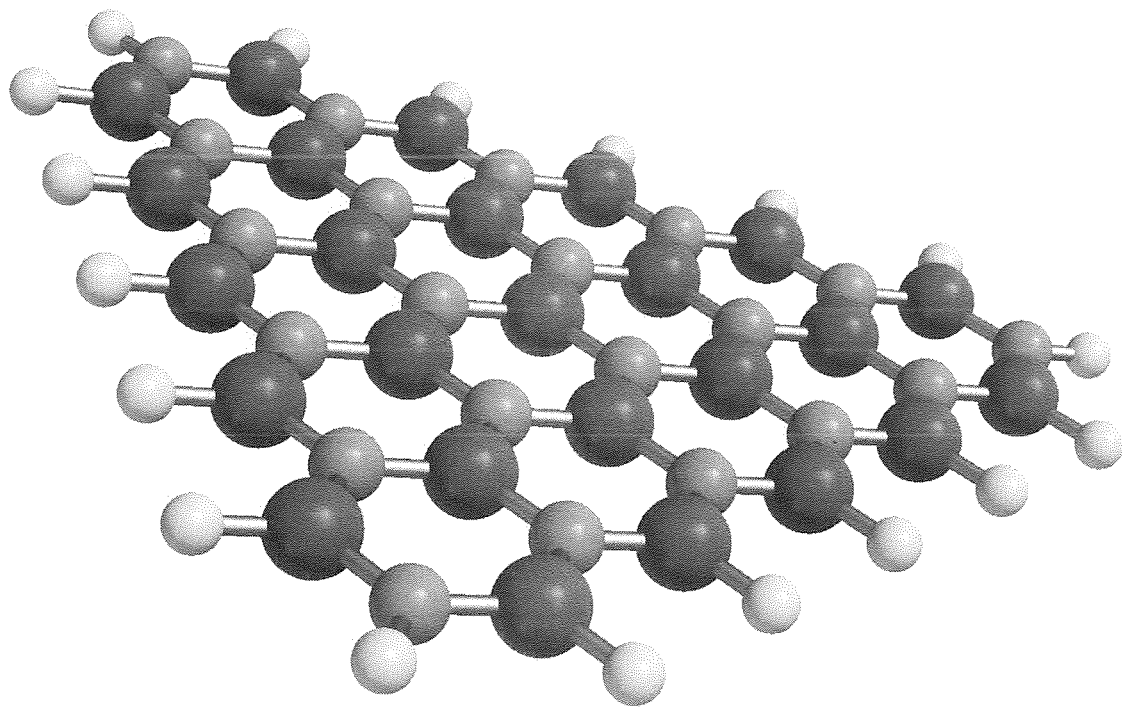
FIG. 4 shows a model of a fragment of hexagonal boron nitride depicting planarity.

Before describing the inventive compositions and processes in detail, it should be understood that the invention is not limited to the specific components, amounts of components, the order of addition of components in the inventive process, or the applications for use set forth herein. The inventions may include other embodiments and may be practiced in various ways, as one skilled in the art would understand from the description.

Terminology used herein is not intended to be limiting. The use of "including", "containing", "constituting", "comprising" or "having" and any other variations thereof is not limited to the items recited or listed and is intended to encompass equivalents and additional items. Use of singular terms are intended to include the plural form.

Numerical ranges described herein include all values from the lowest value to the highest value.

For the purposes of the present invention, the following terms are defined:

In our usage, a "nano-structured particle" or a "nanoparticle" is a particle that possesses structural features having dimensions on the scale of nanometers (such as, for example, the thickness of the clathrate cage). These terms are used interchangeably herein.

Strictly speaking, a nanoparticle is generally considered to be a particle in which all dimensions are less than 100 nanometers, however such particles are often prepared as a distribution of sizes encompassing a range from particles smaller than 100 nm to particles that may be substantially larger. Distributions of particle sizes in which nearly all of the particles are less than 600 nm diameter, and the average particle size is less than about 200 nm diameter are most suitable for jetting. Average particle sizes of less than about 150 nm are particularly useful for jetting applications.

"Gel" means a colloid or solution in which a dispersed phase (solid) combines with a dispersion media (fluid) to form a semi-solid or viscoelastic material.

We use the term "gel" interchangeably with the terms "structured fluid", "structured fluid matrix", or "structured fluid host". With respect to the invention in particular, all of these terms mean and include the semi-solid or semi-rigid gel resulting from the mixing of host vessels (molecules), such as native or modified polysaccharides, cavitands, simple sugars, such as the monosaccharides dextrose, fructose, or glucose, disaccharides, such as sucrose, simple (linear, branched, or cyclic) polyols, such as ethylene glycol, propylene glycol, glycerin, sorbitol, xylitol and the like, crown ethers, aza crowns, cryptands, cyclophanes, oligo- and poly-peptides, proteins, oligo- and poly-nucleotides, or other similar molecules in an acidic dispersing fluid. The use of the term "structure" is simply a reference to the control of the dimensions of void regions (regions without dissolved solid in which particle growth will be constrained), or it may be a higher order structure with liquid crystalline properties characterized by organization of the position and orientations of the dissolved solid.

"Template" refers to the functions/applications of the structured fluid as a form for reducing particle size or constraining the growth of the particle.

"Scaffold" means the support structure that is created by the clathrate cage, limiting agglomeration of the nanoparticles, thereby stabilizing the colloidal dispersion. The clathrate cage also provides points for attachment of other components to the added "guest" solid.

"Clathrate" means a composition in which the molecules of one substance (guest molecules) are physically trapped within the structure of another (host vessel). For purposes of this invention, clathrate also refers to the novel nanoparticle-based colloidal particles created by the addition of a guest solid to the structured fluid host.

The terms "host", "host vessel" and "clathrate cage or shell" are used interchangeably to describe the exterior portion of the clathrate that is trapping the solid in the interior.

The terms "methods" and "processes" are used interchangeably herein.

"Stability" refers to the stability of the interaction between the components of the clathrate (i.e., the trapped particle and the "host vessel"), but it is also used to describe the colloidal stability of the dispersion (i.e., the tendency of the particles to remain dispersed and to not agglomerate). An effort is made to keep this distinction clear within the context of the discussion.

The process is described as a "one step" process. In the context of the invention, "one step" means a one batch mixture comprising the required components, wherein the components may be added all at once or in portions, sequentially/or and at various stages of the process. The term "one step" in referring to the inventive methods means a one batch mixing process that may include several stages or phases where additional components are added to the batch and/or process conditions such as temperature and mixing time are varied.

A feature of the invention is that all the components may be combined into one batch/mixture to achieve the resulting nanoparticles and colloidal dispersions.

Other definitions are set forth throughout the description.

Host Vessels/Molecules: The novel nano-structured particles and colloidal dispersions of the present invention are based upon modifications of polysaccharides, cavitands, simple sugars, disaccharides, simple polyols, and other similarly structured molecules, all described herein, which are known to one skilled in the art to be useful host vessels.

Some classes of compounds possess organizational features within their structure known to promote the formation of strong, non-covalent bonding. These features allow them to play "host" very effectively for particular guest molecules. Prominent among these compounds are certain polysaccharides that adopt specific conformations including hydrophobic regions, defined hydrogen bonding and electrostatic orientations.

Compounds useful in the invention to prepare the structured fluid matrix and reduce the particle size of selected guest solids include but are not limited to certain native polysaccharides, such as amylose, and modified polysaccharides, such as maltodextrin and chitosan, and other similarly structured molecules, as well as related compounds, such as cyclodextrins, calixarene, and cucurbituril. Simple sugars, such as the monosaccharides dextrose, fructose or glucose, disaccharides, such as sucrose, and simple (linear, branched, or cyclic) polyols, such as ethylene glycol, propylene glycol, or glycerin, sorbitol, xylitol and the like, crown ethers, aza crowns, cryptands, cyclophanes, oligo- and poly-peptides, proteins, oligo- and poly-nucleotides, having or that are able to be modified to achieve specific conformations are also thought to be useful for the present invention.

Cyclodextrins, in particular, exhibit these organizational features to a greater degree due to the conformational constraints imposed by their cyclic structure. Cyclodextrins are members of a class of cyclic compounds known as cavitands that include, in addition to cyclodextrin, synthetic molecules with similar properties, such as calixarenes and cucurbiturils, which are considered to be within the scope of the invention.

Host components useful in the invention have been described above. Other similarly structured molecules known to one skilled in the art to be useful host vessels in supramolecular chemistry applications are also within the scope of the invention.

Guest Particles: A wide variety of selected guest solids may be used in the inventive processes. By way of example, the inventive processes have been found to be useful for preparing nano-structured pigment particles and dispersions thereof. Particularly suitable pigments for inclusion as guest particles include without limitation: Pigment Red 122, solid solutions of mixed quinacridones such as Cinquasia® Magenta D 4500 J (solid solution of quinacridones), Solvent Blue 15, Solvent Green 7, Solvent Green 36, Pigment Yellow 74, Pigment Yellow 180, Pigment Yellow 120, or Pigment Red 177, or carbon black or graphite. Other classes of colored pigments include, for example, anthraquinones, phthalocyanine blues, phthalocyanine greens, diazos, monoazos, pyranthrones, perylenes, heterocyclic yellows, quinacridones, and (thio) indigoids. Representative examples of quinacridones include Pigment Orange 48, Pigment Orange 49, Pigment Red 122, Pigment Red 192, Pigment Red 202, Pigment Red 206, Pigment Red 207, Pigment Red 209, Pigment Violet 19 and Pigment Violet 42. Representative examples of anthraquinones include Pigment Red 43, Pigment Red 104 (Perinone Red), Pigment Red 216 (Brominated Pyranthrone Red) and Pigment Red 226 (Pyranthrone Red). Representative examples of perylenes include Pigment Red 128, Pigment Red 149, Pigment Red 168 (dibromoanthanthrone available from Clariant as SCARLET GO), Pigment Red 179, Pigment Red 190, Pigment Violet 19, Pigment Red 189, and Pigment Red 224. Representative examples of thioindigoids include Pigment Red 86, Pigment Red 87, Pigment Red 88, Pigment Red 181, Pigment Red 198, Pigment Violet 36, and Pigment Violet 38. Representative examples of heterocyclic yellows include Pigment yellow 1, Pigment yellow 3, Pigment Yellow 12, Pigment Yellow 13, Pigment Yellow 14, Pigment Yellow 17, Pigment Yellow 65, Pigment Yellow 73, Pigment Yellow 74, Pigment Yellow 151, Pigment Yellow 117, Pigment Yellow 128, Pigment Yellow 138, and Yellow Pigment 155. Other pigments useful in the present invention will be obvious to one skilled in the art.

As another example, the inventive processes are particularly useful to prepare nanostructured particles of two-dimensional materials, such as the inorganic ceramic material hexagonal boron nitride (h-BN). Hexagonal boron nitride is a two-dimensional material, like graphite, but it is much more difficult to achieve an aqueous dispersion of hexagonal boron nitride as compared to graphite. Other boron nitride compounds are within the scope of the invention.

Hexagonal boron nitride (h-BN) consists of layers within which each single atom of boron is covalently bonded to three atoms of nitrogen, and each single atom of nitrogen is covalently bonded to three atoms of boron. Each of these single atom thick layers is bound only weakly to the layer above and to the layer below it by non-covalent forces. This bonding yields a material with 2-dimensional, sheet-like structure analogous and isoelectronic to the structure of graphite. As is the case with graphite, particles, tubes, or rolls composed of only a single or a few layers of h-BN show intriguing properties and are currently the subject of intensive research. The general formula for h-BN is shown below.

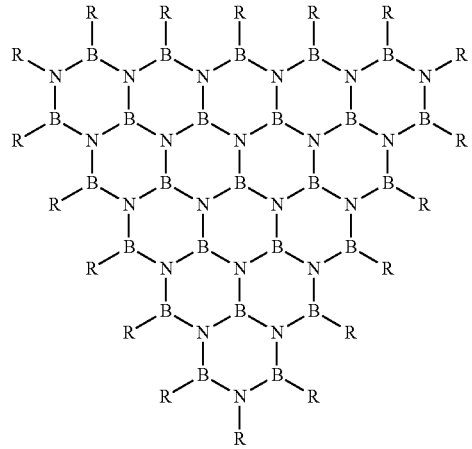

h-BN possesses high thermal stability, chemical inertness, and biocompatibility together with low toxicity. h-BN nanostructured particles have intrinsic utility in diagnostic applications such as boron MRI, and as Active Pharmaceutical Ingredients (APIs) in therapeutic applications such as Boron Neutron Capture Therapy (BNCT). See, for example, Singh, et al., Sci. Rep. 2016; 6: 35535; Ciofani, et al., Nanoscale Res. Lett. (2009) 4:113-121 and sources cited therein. Separately, h-BN is useful as nanocarriers for targeted delivery of other API compositions (Permyakova, et al., J. Phys. Chem. 2017, 121, 28096-28105; Weng, et al., ACS Nano vol. 8, No. 6, 6123-6130, 2014; and sources cited therein). Likewise, h-BN nanostructured particles may also be useful sorbents, carriers, and storage materials for other substances for non-therapeutic applications as diverse as water purification (Lei, et al., Nat. Commun. 2015; 6: 8849) and hydrogen storage (Weng, et al., ACS Nano vol. 7, No. 2, 1558-1565, 2013). They may also improve the properties of structural composites (Wang et al., 2013 J. Phys.: Conf. Ser. 471 012003). As well, they have been proposed to have potential uses for their electronic properties as semi-conductors and also for their optical properties such as luminescence (Wang, et al., J. Am. Chem. Soc. 2008, 130, 8144-8145 and Zhi, et al., J. Am. Chem. Soc. 2005, 127, 15996-15997).

The insolubility and poor dispersibility of h-BN, as compared to graphite, hinders preparation and use of nanostructured h-BN particles (Lei, et al., Nat Commun. 2015; 6: 8849, Weng, et al., ACS Nano vol. 8, No. 6, 6123-6130, 2014). Dilute dispersions of nano-structured h-BN in organic solvents have been prepared that are stabilized by non-covalent associations with polymers (e.g., Zhi, et al., J. Am. Chem. Soc. 2005, 127, 15996-15997). Dilute aqueous dispersions have been stabilized by non-covalent association with smaller, charged molecules (e.g., Wang, et al., J. Am. Chem. Soc. 2008, 130, 8144-8145). The chemical inertness of h-BN renders difficult the preparation of derivatives with improved dispersibility. More dispersible derivatives have been prepared, e.g. by ball milling h-BN together with urea (Lei, et al., Nature Communications 2015; 6: 8849). Nonetheless, persistent challenges remain, including achieving stable, high concentration colloids of uncontaminated nanostructured h-BN. The high level of activity in this field of research demonstrates the continued need for both improved particles and processes for preparing them.

The "scotch tape method" has been applied to prepare nanostructured examples of 2-dimensional materials. The defining property of 2-dimensional materials is that they have strong, covalent bonding between atoms in the plane of each single atom thick layer, but only relatively weak, non-covalent forces binding the layers to one another. The "scotch tape method" proceeds via attachment of an adhesive device (e.g., scotch tape) to the bulk surface of the 2-dimensional material. This allows application of force focused in the direction of the axis perpendicular to the 2-dimensional covalently bonded plane of the material, efficiently breaking cohesive forces between the layers. Sequential application of this technique allows preparation of products such as graphene and analogs with only a single or a few layers and each layer a single atom thick.

In the inventive processes for preparing nanostructured particles of h-BN, a sticky, viscoelastic gel with entrained solid particles is driven by an agitator (mixer). The shearing forces impinging upon entrained particles of a 2-dimensional material in this process result in substantial force applied in the axis perpendicular to the 2-dimensional layers, breaking the cohesive force between the layers and pulling them apart. It has been demonstrated that the inventive process is an efficient technique for preparation of nanostructured particles of 2-dimensional compounds, including but not limited to h-BN.

Lei, et al., described above, described a process for preparing highly water dispersible, nanostructured boron nitride by ball milling hexagonal boron nitride together with urea. They proposed that the —NH2 groups in the urea may react at the edge of the 2-dimensional boron nitride sheets or at defect sites within them to functionalize the boron nitride forming an amino functionalized product with increased water dispersibility.

While not wishing to be bound by theory, with respect to the present invention, it is believed that functionalization might also help to stabilize or participate in the formation of tears within the boron nitride sheet. Such stabilization could promote the reduction of the boron nitride particle size as the sheets "tear". In the application of the inventive processes to form nanostructured particles of h-BN described herein, the —NH2 group-containing amino sugar glucosamine was included, which might likewise react with edges or within the boron nitride sheet to promote tearing and reduction of the size of the boron nitride sheet. Attachment of an amino sugar to the boron nitride particle might also promote the "stickiness" of the boron nitride surface to the gel. It is believed that this "stickiness" may help to anchor the boron nitride within the clathrate and also to more efficiently couple particle size reduction to the shear forces in the mixing gel.

As with other nanostructured particles prepared by the inventive processes, the nanostructured hexagonal boron nitride is formed within a clathrate of material derived from other components included in the process (i.e., acid medium and host compounds, such as glyoxylic acid and β-cyclodextrin, along with glucosamine, and maleic anhydride). The properties of the resultant clathrate yielded aqueous dispersibility of the particles and their resistance to re-agglomeration.

In yet another example of a guest particle, it has been found that the inventive processes can be used to prepare nanostructured particles of thermoplastic materials. Thermoplastic materials soften or melt as inter- and intra-molecular forces weaken with heating. When these materials cool, non-covalent forces within and between the molecules re-assert themselves and the material once again solidifies. Thermoplastics have many uses, including as structural materials and as adhesives. It was discovered that utilizing thermoplastic materials as guest particles alone, or along with other guest particles to form composite nano-structured particles, resulted in colloidal dispersions of nanoparticles having novel applications in a variety of structural and adhesive applications.

The Lac insect of southern Asia exudes a biological, thermoplastic material that forms a protective structure for the insect as it feeds upon their host trees. People living in this region have harvested and processed this material into the refined form, known as shellac, for centuries. Uses for shellac include applications that take advantage of its adhesive and structural properties. Shellac adhesive joins the constituent parts of high-quality musical instruments for example, and the thermoplastic properties of shellac made it the first commercially successful material used to press phonograph records.

It has been found that shellac may be incorporated into the inventive processes to prepare nano-structured particles or incorporated along with other guest particles to form composite nano-structured particles. Composite nanoparticles prepared with shellac and pigment and processed with heating to moderate temperatures (e.g., about 60° C.) showed improved adhesion, fastness, and rub resistance properties compared to nanoparticles not including a thermoplastic component. Notably this improvement extends to semi-porous and non-porous surfaces including coated papers and plastic films.

Other suitable solids for inclusion as guest particles include colorants, dyes, scents, flavors, fragrances, chemicals, both natural and synthetic, including organic, inorganic and mineral, metals and metal ions, pharmaceuticals, biological or biologically derived materials, antibodies, chemical indicators, biological indicators, biological assay materials, such as sensors and analytes, reagents, ceramic materials, thermoplastic materials, and the like. Based on the disclosure herein, one skilled in the art would be able to determine additional suitable solids for use as guest particles.

The Inventive Process: It has been discovered that when the "host" compounds are dissolved or dispersed within certain acidic fluids or other solvents, they form a viscoelastic or semi-solid gel, which is a "structured" fluid matrix having regions within the fluid that act as a template to reduce the particle size of an introduced solid to nanoparticle dimensions or to control the growth of small particles. During and after the formation of these small particles, a clathrate cage forms around the nanoparticle. The structure of this cage is derived from a portion of the gel template. Any excess of the gel template remains free and may be easily purified, filtered or otherwise removed from the clathrate dispersion after the reaction.

The novel nanoparticles of the present invention are prepared by controlling formation of the particles, and thus their size, upon addition of a selected guest solid to a "structured" fluid matrix comprising a gel prepared from a host vessel comprising certain native or modified polysaccharides, cavitands, simple sugars, such as dextrose, fructose, glucose, disaccharides, such as sucrose, and simple (linear, branched, or cyclic) polyols, such as ethylene glycol, propylene glycol, or glycerin, sorbitol, xylitol and the like, crown ethers, aza crowns, cryptands, cyclophanes, oligo- and poly-peptides, proteins, oligo- and poly-nucleotides, or other similarly structured molecules known to be useful host molecules in supra-molecular chemistry, dispersed in a fluid such as a polyphosphoric acid, particularly superphosphoric acid (105%), sulfuric acid (~80 wt. % aq.) or glyoxylic acid (50% aq.). For superphosphoric acid, the percentage greater than 100% indicates the ability to absorb water by hydrolyzing phosphoric anhydride bonds. Other concentrations of these components and other acids and solvents can also be used, provided that they facilitate the formation of the structured fluid matrix.

It is believed that the particle size reduction of the selected guest solid proceeds via larger particles dissolving and then recrystallizing within the template created by the structured fluid. Particle size reduction may be driven in part by increasing the surface area of the selected solid particles within the structured fluid matrix to create more interfaces with the surfaces of the host vessel. Ultimately, the scaffold reduces the particle size of the selected solid upon recrystallization and limits the particle size achieved to nanostructured particles. The nanoparticles are thus captured within the clathrate, wherein the nanoparticles are encompassed by a clathrate cage formed from the fusion of molecules of the host vessel at the surface of the nanoparticles.

Following processing, the nanoparticles thus prepared retain a portion of the structured fluid matrix as a vessel or "host" structure for the added "guest", i.e., selected solid. This host/guest combination is a clathrate cage with a nanoparticle attached to or located within the structure, resulting from trapping the guest particle within, or attachment of the guest particle to, the host vessel. The composition of the clathrate cage is derived from a portion of the particular solid that is dissolved, as the guest, in the structured fluid matrix. Following the quench of the reaction with water (or dry materials), adjustment of pH as required, removal of salts and the other components of the gel not attached to the nanoparticles, a stable colloidal dispersion is achieved. Additional components may be added to the process to stabilize the nanoparticles and resulting colloidal dispersions. Additional components may also be later reacted with the colloidal dispersion for further stabilization or to adjust certain properties of the nanoparticles, such as chroma or shade or affinity or selectivity for a surface, if desired.

In the dispersion, the clathrate is believed to stabilize the dispersion, inhibit agglomeration between guest particles and serve as a scaffold for attachment of other molecules to the surface of the guest particle. These attachments may include charged functional groups that increase zeta-potential, further inhibit agglomeration and enhance the stability of colloidal dispersions prepared from the particles. Additional stabilization components are not required during the process, although it has been found that addition of cyclic anhydrides, dieneophiles, conjugate addition acceptor compounds, lactones or lactams may be added during the process to stabilize the nanoparticles and colloidal dispersions thereof. Similarly, additional steps are not required for stabilization of the colloidal dispersions resulting from the inventive process, although additional stabilization steps may be taken if desired, as further described herein.

Other mechanisms may also contribute to the stability of the colloidal dispersions described herein. In particular, for certain host vessels, discussed below, caramelization may be involved in the stabilization of the resulting nanoparticle colloidal dispersion. Caramelization may be promoted by the acidity and dehydrating conditions resulting from the use of superphosphoric acid and more concentrated sulfuric acid. Acids also have the ability to dissolve solids like pigments, for example, that have very strong intra-molecular attractions between the molecules of the solid, and which are not very soluble in most other solvents. This may be because the acidity tends to weaken certain intra-molecular attractions, such as hydrogen bonds. For this reason, acids may be preferred solvents, although the invention is not so limited.

Extreme caramelization should be avoided because it may result in larger particles and a less stable colloid. Hence, depending on the host vessel used to form the gel, the concentrations of the acids or other solvents may vary. For example, with maltodextrin, if the concentration of sulfuric or other acid is too high, "charring" carbonization will occur, which is a very extreme example of caramelization.

Carbohydrates, in particular, including without limitation, simple sugars, polysaccharides and cyclodextrins, undergo caramelization reactions. These reactions typically proceed at temperatures in excess of 100° C.; however, it is known that they are promoted under acidic and dehydrating conditions that are found, for example, in the reactions in polyphosphoric (superphosphoric 105%) acid, sulfuric acid (80 wt. % aq.), or glyoxylic acid (50% aq.) described herein. It is believed that caramelization may strengthen or contribute to the strength and stability of the resultant clathrate cage structure and may help to increase the colloidal stability of the particle dispersion, by increasing the hydrophilic characteristics of the host vessel surrounding the guest particles. It is also possible that caramelization may introduce new chemical moieties, such as ketones that can serve as "handles" for attachment of other groups to the particle, or it may directly result in the formation of acidic groups on the surface of the vessel surrounding the guest particle that increases the zeta potential and thus stabilizes the colloid. Use of aldehydes, such as glyoxylic acid, may also contribute to and facilitate attachments or linkages between host vessel molecules and guest solids.

While not wishing to be bound by any particular theory, it is believed that the selected host vessel, when dispersed in liquid acid medium (or other solvent), forms regions within the resulting structured fluid matrix wherein particle growth is constrained. The guest material added to the structured fluid may become organized within these regions, both while being dissolved and also while recrystallization occurs such that the particle size is reduced and the $-\Delta G$ (Free Energy change) for the interaction between the guest material and the host region is maximized in an annealing process. This Free Energy change for the interaction between the guest material and the host region connotes non-covalent bonding interactions and attractive forces between them, including non-polar (hydrophobic and Van der Waals), $\pi$-stacking, polar, and hydrogen bonding. The $-\Delta G$ (negative change in free energy denoting a process that will be spontaneous) for this interaction may help to drive the particle size reduction of the guest material so that the contact area between the surfaces of the guest material and the host region is increased. Following a quenching stage, the interactions between the host region and guest material are substantially locked into place.

From another view of the inventive process, the attractive forces between the surface of the guest particle and the structured fluid may be described as adhesive forces between the particle and the fluid. Solutions and dispersions of polysaccharides, and other carbohydrates, including cyclodextrins and even simple sugars and polyols, are widely understood to be "sticky". In addition, the time required for rearrangements of structure within these fluids can lead to viscoelastic behavior wherein the viscosity of the fluid varies depending upon the time scale of the force applied to the fluid. Breaking the adhesion between a particle surface and a viscoelastic or sticky fluid matrix can require more than 10,000 times the amount of energy released in the formation of the adhesive interaction. The reasons for this remain obscure.

Among other contributions, the energy change has been attributed to the separation of molecular entanglements formed between the adhered surfaces, interfacial instabilities, and even cavitation (Zhao, Zeng, Tian, and Israelichvili; PNAS, 2006: Vol. 103, No. 52, 19624-19629). Cavitation is a source of highly focal energy that is very useful for particle size reduction. Recent published work predicted that higher viscosity promotes the inception of cavitation at lower flow velocity (Padrino, Joseph, Funada, Wang, Sirigano; J. Fluid Mech., 2007: Vol. 578, pp. 381-411). This work also cited experimental evidence to support the onset of cavitation at lower flow rates in more viscous fluids.

Prior art technologies to prepare stable colloids of nanoparticles, particularly for jetting, promote cavitation either through fluid flow impingement or in ultrasonic fields. Notably, for many applications in which a colloidal dispersion of small particles is required, high viscosity is undesirable. This is particularly true for colloidal dispersions prepared for jetting applications. It is a feature of the inventive processes that the structured fluid matrix has high viscosity during particle size reduction. In addition, host components of the structured fluid matrix that are not utilized in the formation of the clathrate surrounding the guest particle are easily removed following the quench of the reaction, for example, by membrane ultra-filtration, thus reducing the viscosity. This facilitates the process of reducing particle size easily and efficiently in a high viscosity structured fluid matrix to prepare stable colloids of small particles, while remaining at a suitable viscosity for jetting applications.

Hence, the inventive processes are distinct from prior art processes wherein particle size is reduced in a high viscosity medium and the viscosity remains high in the final colloidal dispersion of particles. The inventive process unexpectedly yields rapid reduction of particle size even at low fluid velocity and is a unique, distinctive technology to reduce particle size by initiating cavitation in a high viscosity structured fluid that is easily rendered into a low viscosity colloidal dispersion of small particles by simple processing, such as dilution and/or membrane ultra-filtration. The inventive stable colloidal dispersions are useful for the preparation of dispersions for jetting and other stable colloidal dispersions of particles.

Much of the energy that is applied to separate adhered surfaces dissipates in the deformation of the bulk material (Ruths and Granick, Langmuir Vol. 14, No. 7, 1804-1814). This deformation can contribute to the breakdown of the cohesive forces that hold the particle together. Reduction of the size of particles entrained within the structured fluid can occur as these attractive forces overcome the cohesive forces within the particle.

It is further known that nano-structures, such as graphene, can be formed by peeling layers off of the surface of a material that is adhered to the surface of another material, such as an adhesive tape. Likewise, the structured fluid may efficiently couple the mixing (mechanical) energy to pull the guest particle apart, which is distinct from typical methods of particle size reduction that break the particle down by physical impact from media or a shock wave. Even relatively slow rates of the flow of the structured fluid may pull the guest particle apart, possibly by focusing the mixing energy to move sequentially along the length of a crystalline phase of the selected guest solid and "unzip" the interactions between the facets of the crystal, thus reducing the particle size. Further, at these slower rates of flow, the host components of the structured fluid have increased time to reorganize at the newly formed particle surface, and to maximize the attractive forces between the host components of the fluid and the guest particle.

Accordingly, the inventive processes also represent distinctive technology that focuses mechanical energy of a reaction to reduce particle size to form a colloid within a condensed phase (the gel) for the preparation of dispersions for jetting and other stable colloidal dispersions of particles, which differs significantly from heretofore described abrasive or shock wave impact processes for particle size reduction. In addition, the chemical properties of the structured fluid matrix, such as for example the pH, may serve to decrease the cohesive properties within the guest particles even when the particles are not dissolved. This may be done, e.g., by weakening hydrogen bonding within the particle, by protonating hydrogen bond acceptors, or by deprotonating hydrogen bond donors making them more susceptible to particle size reduction by this "peeling" process.

In summary, the inventive processes achieve excellent and surprising particle size reduction, without prior media milling, ultra-sonics, or high velocity fluid flow to reduce particle size of a guest solid prior to introduction into the process. They also achieve unexpected high colloidal stability of the resultant nanoparticles, without adding surfactants or polymers or covalently attaching reactive intermediates to the particle surface. While not wishing to be bound by any particular theory, it is believed that unlike the prior art techniques for preparing stable colloids of nanoparticles, particularly for jetting, the inventive processes:

1. Reduce the size of particles by dissolving and recrystallizing them in a structured fluid matrix that constrains their growth and promotes particle size reduction by increased attraction ($-\Delta G$) between the increased surface area of the particles and the host components of the structured fluid.

2. Reduce the size of particles by promoting cavitation, induced by mixing (mechanical) energy in a high viscosity structured fluid even at low fluid velocities.

3. Reduce the size of particles by efficiently coupling mixing (mechanical) energy through attractive interactions between the structured fluid and the particle surface to peel layers from the surface of the particle even at low fluid velocities.

4. Stabilize the increased surface area of the nanoparticles by fusing components of the structured fluid matrix through caramelization, or transglycosylation between sugars, or cross-linking through an acetal to form a clathrate with the particle.

5. Stabilize the colloidal dispersion of the nanoparticles during the process by increasing the zeta potential through charged groups at the surface of the clathrate derived from acidic groups formed by caramelization, charged groups attached to the clathrate through acetals, charged groups attached to the clathrate through other chemistries, or additional components added to the process at the time of particle size reduction and annealing but before quenching.

6. Stabilize the colloidal dispersions resulting from the process by removing acidic materials from the dispersion by a base, or by carboxymethylation of nanoparticles by an acid.

It is a critical feature of the invention that the components forming the structured fluid matrix (i.e. host vessels), which are not strongly bound (non-covalently) to the guest particle, may be separated, such that the final product is a dispersion of nano-structured particles containing a core of guest particles surrounded by a host vessel (the clathrate cage)

formed within the structured fluid matrix. This separation is necessary so that the final product may be obtained with the desired concentration of guest material and in the desired particle size range, and with the desired viscosity, all of which are essential when the particles are being prepared for jetting applications.

Separation may be accomplished, preferably, by a membrane ultra-filtration (diafiltration) process as further described in the examples. It is therefore a feature of this invention that the host vessel components and liquid used to form the structured fluid are able to pass across the ultra-filtration membrane while the clathrate product, i.e., host/guest particles, is retained. The invention provides a structured fluid matrix using selected host vessel components, as described above, many of which are at, or smaller than, the scale of the desired final particles. This is accomplished by selecting host components having the desired scale. However, the invention does not require host components of any particular scale. For this reason, if larger polysaccharides, cavitands or other host vessels in liquid are used to form the structured fluid, their use requires a digestion or other pre-processing step to reduce them to components that will easily pass across the ultra-filtration membrane. This digestion may involve, for example, hydrolysis or other cleavage by oxidative or free radical digestion steps. Care must be taken so that the digestion steps do not interfere with the formation of the nanoparticles and/or degrade or damage the desired properties of the final particles.

For example, starch may be pre-digested to smaller scale components before addition of the guest material, or only the smaller amylose component and not the amylopectin component of starch may be utilized. Alternatively, one can begin with an already modified form of a polysaccharide, such as, for example, maltodextrin. As another alternative, and surprisingly, it has been discovered that much smaller molecules, such as the cavitands (e.g., cyclodextrins, calixarenes, and cucurbiturils), may be used as host vessels to form the structured fluid matrix. Excess maltodextrins or cavitands may then be easily removed by the membrane ultra-filtration described herein, or by other methods known to those skilled in the art.

While particle size reduction by milling or other physical or mechanical techniques may be used in conjunction with the present methods, depending on the guest solid selected, it is typically not required to obtain particle size reduction, except when the dimensions of the molecular components of the guest solid selected for inclusion are much larger than the desired particle size or agglomerated via covalent bonds, as in the case of some carbon blacks. In any event, the particle size reduction occurring prior to introducing the selected solid to the structured fluid matrix does not and is not intended to result in nanoparticles, but rather to facilitate the formation of nanoparticles in the inventive process. It is believed that the inventive process coupled with mechanical energy generated during the process is sufficient to achieve particle size reduction.

The method of preparing the inventive compositions is done in a one batch mixing process, with components being added in sequence at various stages, i.e., gel formation, particle size reduction and annealing, quenching, and colloidal dispersion. Various size reactors may be utilized. Preferably, the reactors include stainless steel, jacketed double arm Sigma mixers. By way of general explanation of the process, an acidic fluid or other solvent medium is mixed (agitated) while adding a modified polysaccharide, cavitand or other host molecules as described above, followed by the addition of the selected guest solid, also with mixing (agitation). This mixture is continually heated and stirred at a set temperature(s) and for set periods of time to achieve particle size reduction and annealing. During the reaction, additional amounts of acid or guest particles may be added, along with other processing aids as further described herein. Aqueous quenching and subsequent filtration yield a pure stabilized product that is a stable nanoparticle-based colloid dispersion. In the event a dry-quench is utilized, nanoparticles formed by the process may be dispersed in water, ideally soft or deionized water, to form the colloidal dispersion. While colloidal dispersion stabilization steps are not necessary, colloidal dispersions may be further stabilized as discussed herein.

Temperatures employed in the process generally range from about 40° C. to 100° C. during component mixing stages and from about 40° C. to 100° C. during the size reduction/annealing stages, although slightly lower or higher temperature ranges (30° C. to 110° C.) may be used and are considered within the scope of the invention. During the process, it is not necessary that only one temperature is utilized for heating the reactor (reactor bath). Depending on the temperature of the reaction, temperatures may be varied during the process as shown in the examples.

Quenching is usually accomplished with the addition of water. The addition of water reduces the solubility of the pigment (or other selected guest solid) in the dispersion, so that the particle size is no longer changing. It may also slow down or stop reactions involving the cyclodextrins or other polysaccharides, such as caramelization.

Other components may be used for quenching, including dry components. Suitable dry quench materials include without limitation sodium carbonate and ammonium carbonate, which also may serve as a base to neutralize acid as further discussed below.

Processing Aids/Improvement of Nanoparticle and Colloidal Stability.

In some aspects, upon completion of the particle size reduction/annealing stage, additional acid components may be added to the reaction, such as sulfuric acid or superphosphoric acid, and the mixture will continue to be heated at a set temperature and stirred for an additional time period. These acid additions may be useful when the primary acid medium used to form the structured fluid matrix (gel) is glyoxylic acid 50%. Glyoxylic acid contains a carboxylic acid directly attached to an aldehyde group. The aldehyde group can be attached to hydroxyl groups on the cyclodextrins or polysaccharides through an acetal linkage, and the formation of the acetal linkage is usually promoted with the addition of some mineral acid, such as sulfuric acid. The rationale for reacting cyclodextrin with glyoxylic acid and later sulfuric acid or superphosphoric acid is that it may promote connections between the cyclodextrins or polysaccharides and thus strengthen the clathrate cage and, further, may promote caramelization of the polysaccharide.

In other aspects, other components may be added at the particle size/reduction annealing stage and prior to the quenching stage as processing aids and/or to improve the stability of the resulting nanoparticles and colloidal dispersions prepared therefrom. Suitable components for addition at this stage include cyclic anhydrides, a dieneophile, conjugate addition acceptor compounds, a lactone, or a lactam compound. Non-limiting examples of such compounds include maleic anhydride, glutaric anhydride, and gluconolactone.

In still other aspects, components may be added at the aqueous quenching stage to stabilize nanoparticles and colloidal dispersions thereof. For example, the aqueous quenching solution may also comprise another component, such as glyoxylic acid or other aldehyde, such as formaldehyde or glutaraldehyde or other polyaldehyde, to aid stabilization by attaching covalently to the clathrate cage and thus improve the stability of the final product. By way of example, the use of glyoxylic acid in quenching facilitates attachment between hydroxyl groups of cyclodextrins, polysaccharides, sugars, or calixarenes through acetal linkages strengthening the clathrate, and also increases the zeta potential on the particle by attachment of a charged carboxylate group to the surface of the particle further stabilizing the dispersion.

Other useful compounds that facilitate attachments and further stabilize the dispersion at the quenching stage or added prior to the quenching stage include: aldehydes, which can react to form hemi-acetals and acetals, hydrazines, hydroxylamines, amines, epoxides, conjugate addition acceptor compounds, nucleophilic conjugate additions, such as acrylic acid or acrylate esters, Michael acceptors, anhydrides, cyclic anhydrides, conjugated dienes, dieneophiles and other compounds that can react with nucleophiles (such as hydroxyl groups), electrophiles (such as carbonyl groups), conjugated dienes (such as furans), or dieneophiles in or on the clathrate cage. These compounds may also be attached to the clathrate cage at a later stage than the quench of the reaction, for example after the pH has been adjusted and also after the particles have been purified, for example by filtration, centrifugation or ultra-filtration. Compounds that are attached to the clathrate may be used to modify the properties of the clathrate. For example, compounds bearing charged groups may be attached to the clathrate to increase the zeta potential of the particle and to help improve the colloidal stability of a dispersion of the particles. Alternatively, groups may be attached that can increase the affinity of the particles for particular substrates such as paper or textiles, or to modulate affinity even more specifically, for example by biotinylation or even by attachment of antibodies.

Base compounds may also be added to neutralize the acid during the quenching stage. Suitable acid neutralizing compounds include sodium, potassium, or other alkali metal carbonates, sodium, potassium, or other alkali metal bicarbonates, sodium, potassium or other alkali metal hydroxides, ammonia or ammonium compounds, and organic amines. Other neutralizing compounds would be well known to one skilled in the art.

Other modifications of the basic process may be included at various stages; however, the key is that the nanoparticles are created by combining components in a one batch reaction mixture. The invention contemplates adding all guest particles at the same time, or multiple additions of guest particles and other components may be added to the batch (mixture) during the process. Process condition modifications, such as temperature changes, additional or other components, or adjusting mixing times may be incorporated at different stages of the reaction to facilitate particle size reduction and to stabilize the nanoparticles and colloidal dispersions thereof.

Colloidal dispersions of nanoparticles formed by the process may be filtered to remove impurities, such as salts from a dry quench, using ultrafiltration techniques. Once filtered, the colloidal dispersions may be further stabilized or their properties modified by reacting the colloidal dispersion with other reactive components, followed by filtration. As one example, colloidal dispersions may be stabilized through reaction with a base, or by carboxymethylation of the nanoparticles using an acid. The chroma or shade of the nanoparticles may be improved by reacting them with a peroxide bond containing compound. In addition, the affinity or selectivity of the nanoparticles for a surface may be improved and changed by reacting the colloidal dispersion with a dihydrazide. A dihydrazide may also be used as a linker to attach the nanoparticles to another molecule that will change the affinity of the nanoparticle for a surface. Suitable bases include without limitation sodium, potassium or other metal hydroxides. Suitable acids for carboxymethylation include without limitation chloroacetic acid and dichloroacetic acid. Suitable peroxide bond containing compounds include without limitation hydrogen peroxide and sodium percarbonate or other peroxide bond containing compounds. Suitable dihydrazides include without limitation adipic acid dihydrazide.

Particle Size Monitoring. The inventive processes may be monitored for particle size at various stages of the process. Particle size measurement during the reaction may be accomplished by removing a tiny portion of the reaction mixture and dispersing it in a dilute solution of ammonium hydroxide. The dispersed particles are then diluted further, if necessary, to allow determination of particle size using a Nicomp PSS model 370 or N3000 instrument. Unless described otherwise, particle sizes set forth herein are the intensity weighted average (Int. wt. avg.) of the gaussian particle size distribution measured on the PSS Nicomp instruments. Particle sizes recorded for finished colloidal dispersions are likewise the intensity weighted average of the gaussian particle size distribution measured on the PSS Nicomp instruments. Evidence of particle size shows that particles are indeed present in the colloidal dispersion.

As is the case for many processes that include particle size reduction, the properties of the particles formed in the inventive processes, as well as those of dispersions prepared from those particles, vary depending in part upon the design, shape, and dimensions of the equipment chosen for the process and the relationship of those parameters to the mass and volume of the reaction mixtures. Likewise, the internal temperatures of the process and the loss of volatiles from the reaction mixtures over the course of the reaction may vary and may impact the results.

The invention is illustrated through several embodiments generally described below and in the examples.

In one preferred embodiment, the gel is prepared by heating a polyphosphoric acid (superphosphoric acid 105%), with agitation (mixing), while adding maltodextrin (MALTRIN M100) with agitation. The clathrate is then formed by adding the selected guest particles to the gel, also with agitation. An alternative embodiment for forming the gel may include using even smaller carbohydrate oligomers, corn syrup, and the like or even simple sugars, such as dextrose, fructose, or glucose, disaccharides, such as sucrose, or polyols such as ethylene glycol, glycerin, sorbitol, xylitol and the like.

In another preferred embodiment, the gel is prepared by heating a polyphosphoric acid (superphosphoric acid 105%), with agitation, while adding β-cyclodextrin (CAVAMAX W7) with agitation. The clathrate is then formed by adding the selected guest particles, also with agitation.

In yet another preferred embodiment, the gel is prepared by heating glyoxylic acid (50%), with agitation, while adding β-cyclodextrin (CAVAMAX W7) with agitation. An alternative embodiment for forming the gel may include using even smaller carbohydrate oligomers, corn syrup, and the like or even simple sugars or polyols such as ethylene glycol, glycerin, sorbitol, etc. The clathrate is then formed by adding the selected guest particles, also with agitation.

In still another preferred embodiment, the gel is prepared by heating a glyoxylic acid (50% aq.), with agitation, while adding sucrose with mixing, followed by addition of superphosphoric acid (105%) during the process if required.

The novel nanoparticle-based clathrates described herein may be used in various applications. Although the primary application described in the examples is for colloidal pigment dispersions, other non-limiting applications of value include, for example:

a. novel therapeutic pharmaceutical compositions, including without limitation nano-technology-based drug treatment and delivery systems, medical diagnostics, medical treatments, biologicals or biologically derived materials, antibodies, and biotechnology-based compositions;

b. delivery and preservation of high value compounds, such as natural colorants, flavors, fragrances, and the like;

c. micro-fluidics;

d. diagnostic materials including without limitation chemical or biological sensors, indicators or assays;

e. chemical extraction and chemical manufacturing processes;

f. materials science, materials jetting and materials manufacturing;

g. electronic applications, including without limitation electronics and electronic materials and jetting and manufacture;

h. synthetic inorganic solids and ceramic materials;

i. materials for structural applications;

j. materials for storage, sorbent and carrier applications; and j. optical materials/applications.

Other applications will be apparent to those skilled in the art.

EXAMPLES

The examples below illustrate the basic inventive processes for preparation of the novel self-assembled nanoparticle-based particles and colloidal dispersions thereof and introduce process variants that provide or achieve improvements in the nanoparticles prepared by the inventive processes.

Example 1. Preparation of a Self-Assembled Nanoparticle Based Colloidal Pigment Dispersion Using Maltodextrin In this example, polyphosphoric acid (superphosphoric acid 105%) was heated, with agitation, and maltodextrin (MALTRIN M-100) was added with agitation. The final mass ratio was approximately 1.06 maltodextrin to 1.00 superphosphoric acid (105%).

At a temperature between about 80° C. and 100° C., color pigment chosen from Pigment Red 122, Solvent Blue 15, or Pigment Yellow 74 was added to the gel with agitation. The final mass ratio was approximately 0.2 pigment to 1.00 superphosphoric acid 105%. Following this, the gel was stirred at elevated temperature for size reduction and annealing for some period of time. Upon completion of the size reduction/annealing period, the reaction was quenched by the addition of water to the reaction mixture.

Example 2. Preparation of a Self-Assembled Nanoparticle-Based Colloidal Pigment Dispersion Using Cyclodextrin In this example, polyphosphoric acid was heated, with agitation, and β-cyclodextrin (CAVAMAX W7) was added with agitation.

The final mass ratio was approximately 1.06 β-cyclodextrin to 1.00 superphosphoric acid 105%. At a temperature between about 40° C. and 60° C., color pigment chosen from Pigment Red 122, Solvent Blue 15, Solvent Green 7, Solvent Green 36, or Pigment Yellow 74 was added to the gel with agitation. The final mass ratio was approximately 0.2 pigment to 1.00 superphosphoric acid 105%. Following this, the gel/pigment mixture was stirred at elevated temperature for size reduction and annealing for some period of time. Upon completion of the size reduction/annealing period, the reaction was quenched by the addition of water to the reaction mixture or by the addition of the reaction mixture to water.

Example 3. Preparation of a Self-Assembled Nanoparticle-Based Colloidal Dispersion of Pigment Using Cyclodextrin In this example, glyoxylic acid (50%) was heated, with agitation, while adding β-cyclodextrin (CAVAMAX W7) with agitation.

The final mass ratio was approximately 1.99 β-cyclodextrin to 1.00 glyoxylic acid (50%) aqueous. At a temperature of between about 40° C. to about 60° C., Pigment Yellow 180 was added to the gel fluid with agitation. In this specific example, the final mass ratio was approximately 0.083 pigment to 1.00 glyoxylic acid (50%) aqueous. Following this, the gel/pigment mixture was stirred at elevated temperature for size reduction and annealing for some period of time. Upon completion of the size reduction/annealing period, 0.9 parts (relative to 1.00 part of glyoxylic acid (50%) aqueous) of concentrated sulfuric acid (about 93-98%) was added to the reaction, stirred, and heated at 60° C. for an additional 6 hours prior to quenching by the addition of water.

Example 4. Particle Size Reduction by Milling of Carbon Black

The process of example 3 was modified to include particle size reduction by milling in the case of carbon black as the selected solid/pigment.

Example 5. Preparation of a Self-Assembled Nanoparticle-Based Colloidal Pigment Dispersion Using Cyclodextrin The Process of example 2 was modified to include a final mass ratio of approximately 0.4 color pigment chosen from Pigment Red 122, Cinquasia® Magenta D 4500 J, Solvent Blue 15, or Pigment Yellow 180 to 1.00 superphosphoric acid 105% to approximately 1.06β-cyclodextrin. Following this, the gel/pigment mixture was stirred at elevated temperature for size reduction and annealing for some period of time. Upon completion of the size reduction/annealing period, the reaction was quenched by the addition of the reaction mixture to water.

Example 6. Preparation of a Self-Assembled Nanoparticle-Based Colloidal Pigment Dispersion Using Cyclodextrin The Process of example 3 was modified to include a final mass ratio of approximately 1.99 β-cyclodextrin to 1.00 glyoxylic acid (50%) aqueous to 0.25 color pigment chosen from Pigment Yellow 180, Pigment Yellow 120, or Pigment Red 177 to 1.00 glyoxylic acid (50%) aqueous. Following this, the gel/pigment mixture was stirred at elevated temperature for size reduction and annealing for some period of time. Upon completion of the size reduction/annealing period, 1.35 parts (relative to 1.00 part of glyoxylic acid (50%) aqueous) of concentrated sulfuric acid (about 93-98%) was added to the reaction, stirred, and heated at 60° C. for an additional 4 hours prior to quenching by the addition of the reaction mixture to water.

Example 7. Preparation of a Self-Assembled Nanoparticle-Based Colloidal Pigment Dispersion Using Cyclodextrin The Process of example 3 was extended to include addition of approximately 0.5 parts glacial acetic acid (relative to 1.00 part of glyoxylic acid (50%) aqueous) to the reaction mixture.

In the above examples, quenching was performed by the addition of water or by the addition of the reaction mixture to water. As set forth herein, dry quenching may be used. The aqueous quenching solution may also comprise another component, such as glyoxylic acid or other aldehyde such as formaldehyde or glutaraldehyde or other polyaldehyde, to improve the stability of the final product, for the reasons discussed above. Other acids may be added to the quenching solution as well. The quenching water may also contain a base to help neutralize the acidic mixture, such as sodium carbonate or sodium hydroxide.

The reaction mixtures resulting from the addition of the pigments to the gel may, after the size reduction/annealing period, continue to be mixed at a set temperature for a set duration until they are mixed into a larger volume of water.

After the final quench of the reaction mixtures, membrane ultra-filtration was performed to remove components of the structured fluid matrix that were not incorporated into the nanoparticles and other impurities, while retaining the nanoparticles. Purification helped to stabilize the dispersions.

Following membrane ultra-filtration, larger and less stable particles were removed from the dispersion, by settling and decantation, centrifugation, filtration or by some combination of these. The dispersions thus prepared showed excellent colloidal stability.

Inks prepared using the above colloidal dispersions of organic color pigments demonstrated excellent jetting properties, which were demonstrated using an HP B 8850 A3 thermal pigment printer.

Example 8—Analysis of Composition

Data (see Tables 1-3 below) obtained by the use of self-dispersed copper phthalocyanine prepared according to example 2 in a gel of β-cyclodextrin in superphosphoric acid (105%) indicated that very little phosphate or polyphosphate remained attached to the nano-structured particles formed using the gel. The spectroscopic data indicated that the surface of the particles was characterized by a high content of highly oxygenated carbon, including ketones and carboxylic acid. Hence, it is believed, and the data supports, that the reaction promoted a caramelization between the cyclodextrin molecules forming the clathrate cage around the particle. Carboxylic acids formed by the process may also be a critical factor contributing to the stability of colloidal dispersions of these particles. Data from TOF-SIM have been interpreted to show the absence of un-modified β-cyclodextrin. This finding helped to distinguish the inventive process from the prior art.

Bulk Particle Element Concentration [PPM Wt.]
C~62 wt. %
N 14 wt. %
O 5.2 wt. %
S<10 PPM
H 3.1 wt. %
C, S determined by Combustion-IR
N, H determined by IGF-TC
O determined by IGF-NDIR

TABLE 1

Particle Surface Atomic Concentrations (in %) by XPS[a]

| Sample | C | N | O | Na | S | Cu | N/Cu |
|---|---|---|---|---|---|---|---|
| Self-Dispersed Cu Phthalocyanine | 73.6 | 14.8 | 8.5 | 0.7 | 0.1 | 2.3 | 6.5 |
| Cu phthalocyanine powder | 74.8 | 19.9 | 2.3 | — | — | 3.0 | 6.6 |

[a] Normalized to 100% of the elements detected. XPS does not detect H or He.
[b] A dash line indicates the element is not detected.

TABLE 2

Carbon Chemical States (in % of Total C) by XPS

| Sample | C—C, H | CN2 | C—O | C=O/O—C—O | C2NCu | O—C=O | Shake-up* |
|---|---|---|---|---|---|---|---|
| Self-Dispersed Cu Phthalocyanine | 57 | 19 | 7 | 4 | 3 | 2 | 8 |
| Cu phthalocyanine powder | 67 | 23 | — | — | 4 | — | 7 |

*The Shake-up structure in a spectrum is resultant of a π→π* transition often indicative of aromaticity.

TABLE 3

Oxygen Chemical States (in % of Total O) by XPS

| Sample | C=O | C—O | H2O |
|---|---|---|---|
| Self-Dispersed Cu Phthalocyanine | 12 | 77 | 11 |

Example 9—Analysis of Composition

Data (see Tables 4-6 below) obtained by the use of self-dispersed Pigment Yellow 180 prepared according to example 6 in a gel of β-cyclodextrin in glyoxylic acid (50% aqueous) indicated that the surface of the particles was characterized by a high content of highly oxygenated carbon, including ketones and carboxylic acid. Hence, it is believed, and the data supports, that the reaction promoted an acetal formation between glyoxylic acid and/or caramelization between the cyclodextrin molecules forming the clathrate cage around the particle. Carboxylic acids formed by the process may also be a critical factor contributing to the stability of colloidal dispersions of these particles. Data from TOF-SIM have been interpreted to show the absence of un-modified β-cyclodextrin. This finding helped to distinguish the inventive process from the prior art. TOF-SIM did detect a significant peak attributed to glyoxylic acid.

TABLE 4

Atomic Concentrations (in atomic %)[a]

| Sample | C | N | O | Na | Cl |
|---|---|---|---|---|---|
| Self-Dispersed Pigment Yellow 180 | 73.8 | 10.5 | 14.9 | 0.8 | 0.1 |

[a]Normalized to 100% of the elements detected. XPS does not detect H or He.

TABLE 5

Carbon Chemical States (in % of Total C)

| Sample | C—C/ C—H | C—O/ C—N | C=O/ O—C—N | O=C—O |
|---|---|---|---|---|
| Self-Dispersed Pigment Yellow 180 | 70 | 20 | 8 | 2 |

TABLE 6

Oxygen Chemical States (in % of Total O)

| Sample | C=O | C—O | $H_2O$? |
|---|---|---|---|
| Self-Dispersed Pigment Yellow 180 | 53 | 45 | 2 |

Examples 10-24 Additional Reactor Experiments

The examples below illustrate development of the inventive process to accommodate larger concentrations of guest particles and the use of other components for commercial application of the inventive process. Higher capacity equipment was utilized to accommodate increases in viscosity resulting from use of larger concentrations of components.

In the examples below, concentrations of components are expressed in mass "units" relative to each other, i.e., mass ratio. Mass "units" shall mean and include grams, kilograms or pounds. The same mass "unit" is used consistently within each example.

With respect to time points described in the examples, all times are measured from the time at which a guest compound (solid) is introduced into the process unless otherwise specified.

Temperatures employed range from about 30° C. to about 110° C. Temperature adjustments may be made during the inventive processes depending on conditions encountered or desired during the reaction, such as viscosity and tackiness, among others.

Example 10: Reactor Experiments—β-Cyclodextrin Gel in Polyphosphoric Acid

The general process utilized a reactor having a stainless steel, jacketed double-arm Sigma mixer, which was heated with a bath. A polyphosphoric acid was added to the reactor with mixing. β-cyclodextrin was added to the mixing polyphosphoric acid in portions and mixed to form a gel.

Example 11: β-Cyclodextrin Gel Formed in Glyoxylic Acid Solution or Melted Glyoxylic Acid Hydrate In another process, the same type of reactor as in Example 10 was utilized. A glyoxylic acid solution in water or melted glyoxylic acid hydrate was added to the heated reactor with mixing. β-cyclodextrin was added to the mixing glyoxylic acid solution or melted glyoxylic acid hydrate in portions and mixed to form a gel.

Example 12: Gel and Clathrate Formation and Particle Size Reduction of a Quinacridone Semiconductor Pigment Red 122

A gel was formed using the process of Example 10, wherein the reactor jacket was heated with a bath at about 60° C., using a mass of added cyclodextrin of about 5 units and a mass of added polyphosphoric acid of about 10 units. The polyphosphoric acid used was superphosphoric acid 105%.

10 units of quinacridone Pigment Red (PR) 122 was added to the gel in five portions of 2 units each with approximately 10 minutes of mixing between each addition. Following each addition, the sides of the mixer were scraped to remove adhering material. Following complete addition of all the pigment, the sides were again scraped, and the reaction was mixed for an additional 10 minutes.

Thereafter, a portion of gluconolactone with mass equal to 2.5 units was added with mixing to the reaction mixture and mixed for 15 minutes, following which the first sample was removed to check particle size.

Particle size was measured as discussed above. The particle size distribution measured on the PSS Nicomp instrument dropped to below 190 nm during about 3 hours of mixing at which time the rate of particle size reduction appeared to slow down. When this occurred, a portion of maleic anhydride with mass equal to 2.5 parts was added with mixing to the reaction mixture.

About 1 hour following the maleic anhydride addition, the temperature of the bath was raised to 70° C. The temperature of the reaction mixture measured using an infrared thermometer was about 82° C. to 86° C., presumably principally due to mechanical heating of the reaction mixture. About 6 to 8 hours from the beginning of the reaction, the mixing speed was adjusted to allow the temperature of the reaction mixture to remain stable at about 82° C. to 86° C.

The particle size was monitored as described at intervals until it began to show some increase at which point the reaction was quenched as set forth in Example 13.

Example 13: Dry quench of reaction of β-cyclodextrin gel in poly-phosphoric acid with the PR (Pigment Red) 122 clathrate by sodium carbonate addition The reaction gel (mixture) of Example 12 was quenched by the careful addition of dry sodium carbonate to the reaction mixture with a mass equal to about 15 units. The reaction mass was mixed carefully with the added sodium carbonate and then unloaded from the mixer. The product obtained can be stored in this dry form for an extended period before being dispersed as discussed below.

Example 14: Dispersion of PR122 Clathrate Gel into Water and Desalting by Ultra-Filtration (UF)

The quenched gel of Example 13 was dispersed carefully in portions into water, ideally soft or deionized (DI) water. It was observed that the gel may foam while it was being dispersed. To increase the rate at which the particles from the gel were dispersed, additional base was added. The dispersion may be filtered, for example with a bag filter. Salt was removed from the dispersion on an ultra-filtration system (UF), one example of which is a tubular ultra-filtration system prepared by membrane specialists. The salt was removed by diafiltration on the UF, and the particle size was monitored. Volume loss across the membrane was replaced with soft or deionized water. After the conductivity of the solution permeating across the UF membrane dropped below a conductivity about 0.3 mS (milli Siemens), the decrease of which indicated the removal of salt, the dispersion was concentrated to about 10% to 15% solids.

Example 15: High pH Treatment of PR122 Colloidal Dispersion

The pH of the colloidal dispersion of Example 14 diluted to about 5% to 10% solids was raised until the pH was stable for about 15 minutes at pH 12 or slightly above using 50% sodium hydroxide solution. The dispersion was kept at this high pH for 18 hours. The dispersion was then diafiltered on UF until the conductivity of the permeate was below 0.1 mS and had very little color.

Example 16: Hydrogen Peroxide Treatment of PR122 Colloidal Dispersion

The dispersion of Example 15 was again adjusted to about 5% to 10% solids by dilution or concentration on UF. With agitation, the pH was adjusted to 11 to 11.5 using 50% sodium hydroxide solution. Other bases may be used to adjust pH. A portion of about 30% to 38% hydrogen peroxide having about 0.5 times the mass of pigment present was then added and mixed for about 15 minutes, following which the mixture was allowed to stand without agitation for about 5 hours. The dispersion was then diafiltered using deionized water while maintaining the pH above 8. As the conductivity of the permeate dropped, the dispersion was concentrated. Diafiltration on the UF was continued until the conductivity of the permeate dropped below 0.1 mS at about 15% solids, and the permeate became very light in color. At this time, the concentration may be adjusted, and the dispersion may be removed from the UF. The colloidal dispersion may also be coarse filtered and filtered with submicron filters and preserved with a biocide such as benzisothiazolinone (BIT).

Example 17: Gel and Clathrate Formation and Particle Size Reduction of a Metallized Macrocycle Pigment Blue 15:4 (Copper Phthalocyanine or PB)

A gel according to the process of Example 10 was formed, wherein the reactor jacket was heated with a bath at about 60° C. A mass of cyclodextrin of about 5 units was added, and a mass of a first polyphosphoric acid charge of about 4 units was added. 2.5 units of gluconolactone was then added, and the reaction mixture was mixed for about 15 minutes. The polyphosphoric acid used was superphosphoric acid 105%. For this example, additional polyphosphoric acid was added to the mixture in subsequent portions as discussed below.

A mass of Pigment Blue 15:4 equal to about 2.5 units was added followed by about 10 minutes of mixing, followed by addition of another portion of polyphosphoric acid equal to about 1 part. The mixture was then mixed for about 5 minutes or until the power load on the agitator became stable.

A second portion of 2.5 units of Pigment Blue 15:4 was then added to the reaction and mixed. The power to the agitator was adjusted until the load on the agitator became stable for 5 minutes, and then the power to the agitator was adjusted to full for an additional 5 minutes of mixing. At that time, another portion (charge) of polyphosphoric acid equal to about 1 part was added and was mixed for about 5 minutes or until the power load on the agitator became stable.

A third portion of 2.5 parts of Pigment Blue 15:4 was then added to the reaction and mixed. The power to the agitator was adjusted until the load on the agitator became stable for 5 minutes, and then the power to the agitator was adjusted to full for an additional 5 minutes of mixing. At that time, another portion of polyphosphoric acid equal to about 1 part was added, and the reaction was mixed for about 5 minutes or until the power load on the agitator became stable.

A fourth portion of 2.5 units of Pigment Blue 15:4 was then added to the reaction and mixed. The power to the agitator was adjusted until the load on the agitator became stable for 5 minutes, and then the power to the agitator was adjusted to full for an additional 5 minutes of mixing.

Following each of the above additions, the sides of the mixer were scraped to remove adhering material. Following complete addition of all the pigment, the sides were again scraped, and the reaction mixed for an additional 10 minutes.

The particle size was monitored as described at intervals until it dropped below about 110 nm or stopped reducing in size. At that time, a portion of maleic anhydride equal to 2.5 units was added to the reaction and the temperature bath was adjusted to maintain an internal reaction temperature of about 82° C. to about 86° C. If necessary, the rate of the mixing can be adjusted to maintain the temperature range. The particle size was monitored at intervals.

At about 24 hours to 27 hours after the start of the reaction, the internal temperature and the particle size were observed to increase. At that time, the reaction was quenched dry with the addition of sodium carbonate to the reactor as discussed below.

Example 18: Dry Quench of Reaction of β-Cyclodextrin Gel in Polyphosphoric Acid with PB (Pigment Blue) 15:4 Clathrate by Sodium Carbonate Addition The reaction gel (mixture) of Example 17 was quenched by the careful addition of about 10 parts dry sodium carbonate to the reaction. The reaction mass (gel or mixture) was mixed carefully with the added sodium carbonate and then unloaded from the mixer. If required, additional sodium carbonate may be added to help displace the entire gel mass from the reactor. The quenched product may be stored for an extended period before being dispersed.

Example 19: Dispersion of PB 15:4 Clathrate Gel into Water and Desalting by Ultra-Filtration (UF)

The quenched gel of Example 18 was added carefully in portions into water, ideally soft or deionized water. Although not required, the gel was allowed to sit for about an hour to wet out before beginning mixing. It was observed that the gel may foam while it was being dispersed. If necessary additional base may be added to increase the rate at which the particles from the gel are dispersed. The dispersion may be filtered, for example with a bag filter. Salt was removed from the dispersion on an ultra-filtration system (UF), such as a tubular, ultra-filtration systems prepared by membrane specialists. The salt was removed by diafiltration on the UF, and the particle size was monitored. Volume loss across the membrane was replaced with soft or deionized water. After the conductivity of the solution permeating across the UF membrane dropped below about 0.3 mS, the dispersion was concentrated to about 10% to 15% solids.

Example 20: High pH Treatment of PB 15:4 Clathrate Colloidal Dispersion

The pH of the colloidal dispersion of Example 19 diluted to about 5% to 10% solids was raised until the pH was stable for about 15 minutes at pH 12 or slightly above using 50% sodium hydroxide solution. Other bases may be used to adjust pH. The dispersion was kept at this high pH for 18 hours. The dispersion was then diafiltered on UF until the conductivity of the permeate was below 0.1 mS and had very little color.

Example 21: Hydrogen Peroxide Treatment of PB 15:4 Clathrate Colloidal Dispersion The dispersion of Example 20 was adjusted to about 5% to 10% solids by dilution or concentration on UF. With agitation, the pH was adjusted to 11 to 11.5 using 50% sodium hydroxide solution. A portion of about 30% to 38% hydrogen peroxide having about 0.5 times the mass of pigment present was then added followed by mixing for about 15 minutes. Thereafter, the mixture was allowed to stand without agitation for about 5 hours. The dispersion was then diafiltered using deionized water while maintaining the pH above 8. As the conductivity of the permeate dropped, the dispersion was concentrated. Diafiltration on the UF was continued until the conductivity of the permeate dropped below 0.1 mS at about 15% solids and the permeate became very light in color. At this point, the concentration may be adjusted, and the dispersion may be removed from the UF. The colloidal dispersion may also be coarse filtered and filtered with submicron filters and preserved with a biocide such as BIT.

The dispersion of this example showed good colloidal stability at room temperature and under conditions of accelerated stability testing of about 60° C. to 70° C.

Example 22: Gel and Clathrate Formation and Particle Size Reduction of a Benzimidazalone Pigment Yellow (PY) 180 in 50% Aqueous Glyoxylic Acid with β-Cyclodextrin and Polyphosphoric Acid A gel was formed according to the process as set forth in example 11, wherein the reactor jacket was heated with a bath at about 60° C. A mass of 50% aqueous glyoxylic acid at about 14.2 units and a mass of β-cyclodextrin at about 28.4 units was added.

After about 10 minutes, 7.6 units of Pigment Yellow 180 was added with continued mixing. Thereafter additional portions of Pigment Yellow 180 were added, with the additions being separated by about 10 minutes, as follows: 7.2 units of Pigment Yellow 180 added with continued mixing; another 6.8 units of Pigment Yellow 180 added 10 minutes later with continued mixing; another 6.8 units of Pigment Yellow 180 added 10 minutes later with continued mixing. Mixing was then maintained in the sealed reactor for about 2 hours and 10 minutes while maintaining the bath temperature at about 60° C. As required, mixing rate may be adjusted to maintain the reaction temperature at about 85° C.

After that time, about 2.2 units of a polyphosphoric acid (superphosphoric acid 105%) was added to the reaction. The reaction vessel was sealed again and mixed for about another 1 hour and 40 minutes, at which time another 1 part of superphosphoric acid 105% was added with mixing. After approximately 35 more minutes of mixing, another 1.5 units of superphosphoric acid 105% was added, followed in approximately one hour by addition of 6.4 units of superphosphoric acid 105% with mixing. After approximately 30 additional minutes of mixing, the reactor was opened, and the sides were scraped to remove reaction mixture adhering to the sides. The reactor was then sealed, and the bath temperature raised from 60° C. to 80° C. The reaction was mixed for another 17 hours. The reactor was opened and an additional 11.1 units of superphosphoric acid 105% were added, followed by scraping the reactor sides to remove reaction mixture adhering to the sides. The reactor was again sealed and mixed for about another 6 hours and 20 minutes at which time about 7 units of maleic anhydride were added to the reaction mixture. After addition of the maleic anhydride, the reaction mixture was then mixed for about another 17 hours and 50 minutes. At the end of mixing, a small sample of the reaction mixture was removed. Particle size was tested as described above, with the result being about 150 nm.

Example 23: Dry Quench of β-Cyclodextrin Gel in 50% Glyoxylic Acid with Pigment Yellow 180 Clathrate and Polyphosphoric Acid by Sodium Carbonate Addition The reaction mixture (gel) of Example 22 was quenched by the careful addition of about 18 units dry sodium carbonate to the reaction. The reaction mass was mixed carefully with the added sodium carbonate and then unloaded from the mixer. If required, additional sodium carbonate may be added to help displace the entire gel mass from the reactor. The dry quenched product may be stored for an extended period before being dispersed.

Example 24: Dispersion of PY (Pigment Yellow) 180 β-Cyclodextrin-Derived Clathrate Gel into Water and Desalting by Ultra-Filtration (UF)

The quenched gel of example 23 was added carefully in portions into water, ideally soft or deionized water. About 1100 parts water to the gel of Example 23 yielded a good dispersion for ultra-filtration. It was observed that the gel may foam while it was being dispersed. Additional base may be added to adjust the pH into the range of about 5 to 8 for ultra-filtration and to improve the colloidal stability of the dispersion. Salts were removed from the dispersion by diafiltration on the UF, and the particle size was monitored. Volume loss across the membrane was replaced with soft or deionized water. After the conductivity of the solution permeating across the UF membrane dropped below about 0.1 mS, the dispersion was concentrated to about 8% to 9% solids. At this point, the particle size was measured as described above at about 150 nm.

Example 25: High pH Treatment, Filtrations and UF of PY 180 Colloidal Dispersion The pH of the colloidal dispersion of Example 24 at about 8% to 9% solids was raised until the pH was stable for about 15 minutes at pH 12 or slightly above using 50% sodium hydroxide solution. Other bases may be used to adjust pH. The dispersion was kept at this high pH for about 1.5 to 2 hours. After that time, a filtration aid (e.g., dicalite speedplus) was added to the dispersion with mixing and then the dispersion was filtered to clarify on a pre-coated filter. Following clarification, the dispersion was diafiltered on UF until the conductivity of the permeate was below 0.2 mS and had very little color. Water removed by diafiltration was replaced in the dispersion with deionized water. The conductivity was dropped to below about 150 nm and the pH to below about 10. If desired, the dispersion may be further improved by additional filtrations through cartridge filters such as Pall Claris filters, Pall Profile II or III depth filters, and Pall Glass cartridge filters. The filtered dispersion may then be preserved by the addition of an antimicrobial such as BIT. The particle size achieved was measured as described above at below (less than) about 150 nm. This dispersion showed good colloidal stability at room temperature and under conditions of accelerated stability testing at about 60° C. to 70° C.

Example 26: Sucrose Gel in Glyoxylic Acid Solution or Melted Glyoxylic Acid Hydrate As a general process for using sucrose as the host vessel, a reactor comprising a jacketed double arm Sigma mixer was heated. A glyoxylic acid solution in water or glyoxylic acid hydrate was added to the reactor with mixing. Sucrose was added to the mixing glyoxylic acid solution or melted glyoxylic acid hydrate in portions and mixed to form a gel.

Example 27: Gel and Clathrate Formation and Particle Size Reduction of a Benzimidazalone Pigment Yellow 180 in 50% Aqueous Glyoxylic Acid with Sucrose and Polyphosphoric Acid A gel using the process described in Example 26 was formed wherein the reactor jacket was heated with a bath at about 50° C. A mass of 50% aqueous glyoxylic acid of about 36 units and a mass of sucrose of about 20 units was added. Components were mixed to form a gel.

After about 5 minutes, 50 units of Pigment Yellow 180 was added with continued mixing, followed by addition in another 5 minutes of another 25 units of Pigment Yellow 180 with continued mixing. Another 25 units of Pigment Yellow 180 was added ten minutes later with continued mixing. After about 10 more minutes, about 8 units of a polyphosphoric acid (superphosphoric acid 105%) was added to the reaction. The reactor was sealed and mixed for about another 5 minutes, at which time another 6 units of superphosphoric acid 105% was added with mixing. Mixing was then maintained in the sealed reactor while maintaining the bath temperature at about 50° C. If required, mixing rate or bath temperatures may be adjusted to maintain the reaction temperature below about 92° C. After about 1 hour and 20 minutes another 4 parts of superphosphoric acid 105% was added with mixing. Mixing was then maintained in the sealed reactor while maintaining the bath temperature about 50° C. and adjusting mixing rate as required to maintain the reaction temperature below about 92° C. After about 50 minutes, another 6 parts of superphosphoric acid 105% was added with mixing. After about 1 hour of additional mixing, another 10 units of superphosphoric acid 105% was added with mixing, and then after 35 more minutes, 12 units of maleic anhydride was mixed into the reaction. About 48 minutes later, a sample of the reaction mixture was taken. The particle size was tested as described above at below (less than) about 135 nm. After about another 16 hours, the reaction gel was cooled to about 60° C., and then dry quenched with the careful addition of about 39 units of sodium carbonate added to the reactor with mixing. The dry-quenched gel was unloaded from the reactor.

Example 28: Dispersion of PY 180 Sucrose-Derived Clathrate Gel into Water and Desalting by Ultra-Filtration (UF)

The quenched gel of Example 27 was added carefully in portions into about water, ideally soft or deionized water. The gel was dispersed and then purified and desalted by diafiltration on the ultra-filter. The particle size of the desalted colloidal dispersion was measured at about 140 nm. This dispersion showed good colloidal stability at room temperature and under conditions of accelerated stability testing at about 60° C. to 70° C.

Example 29: Gel and Clathrate Formation and Particle Size Reduction of a Benzimidazalone Pigment Yellow 180 in 50% Aqueous Glyoxylic Acid with β-Cyclodextrin and Sucrose A gel according to the process set forth in Example 11 was formed wherein the reactor jacket was heated with a bath at about 60° C. A mass of β-cyclodextrin of about 1 unit and a mass of 50% aqueous glyoxylic acid of about 3.6 units was added to the reactor to form the gel. 1 unit of sucrose was then added to the gel with mixing. After about 8 minutes, 2.4 units of Pigment Yellow 180 was added with continued mixing. After about 6 minutes, another 2.4 units of Pigment Yellow 180 was added with continued mixing. After about 6 minutes, 1 unit of a polyphosphoric acid (superphosphoric acid 105%) was added with continued mixing. After about 4 minutes, another 2.4 units of Pigment Yellow 180 was added with continued mixing. After about 6 minutes, another 2.4 units of Pigment Yellow 180 was added with continued mixing. After 30 minutes, 1.25 units of superphosphoric acid 105% was added with mixing. Four hours and 23 minutes following the first superphosphoric acid 105% addition, the bath temperature was 64.2° C., and the reactor temperature was measured with an IR thermometer at 84.4° C. during this time, the reactor was opened at intervals and material adhering to the inside of the reactor was scraped back into the reaction mass (mixture). Five hours and 20 minutes after the first superphosphoric acid addition, another 3 units of superphosphoric acid was added with mixing. Twenty-two hours and 50 minutes following the first superphosphoric acid addition, 2.5 units of maleic anhydride was added with mixing. Six hours and 10 minutes after the maleic anhydride addition, the reaction mixture was dry quenched by mixing with 3 parts of dry sodium carbonate. A small sample was removed, and particle size was tested. The particle size measured as described above at 149.8 nm (intensity weighted average).

Example 30: Gel and Clathrate Formation and Particle Size Reduction of the Inorganic Ceramic Material Hexagonal Boron Nitride Colloidal dispersions of nanoparticles of hexagonal boron nitride were prepared as set forth below.

Run 1.

A reactor comprising a jacketed double arm sigma mixer was heated. A 125 g portion of 50% glyoxylic acid solution in water was added to the reactor. The jacket was heated with a heating bath set to about 50° C. A 125 g portion of β-cyclodextrin is added to the mixing glyoxylic acid solution in parts and allowed to mix to form a gel over about 4 minutes. Following formation of the gel, a 125 g portion of hexagonal boron nitride (325 mesh, Alfa Aesar) was added with mixing over about 20 minutes. The lid to the reactor was removed periodically, and the sides were scraped as needed. About 70 minutes following the addition of the hexagonal boron nitride to the reaction, the setpoint for the bath was increased to about 60° C. About 2 hours after the addition of the hexagonal boron nitride to the reaction, 21.4 g of superphosphoric acid 105% was added to the reaction. About 17 hours and 20 minutes after the addition of the hexagonal boron nitride to the reaction, the bath temperature setpoint was reset to about 50° C. About 17 hours and 40 minutes after the addition of the hexagonal boron nitride to the reaction, 30.0 g of glucosamine sulfate was added to the reaction with mixing. At about 21.5 hours after the addition of the hexagonal boron nitride to the reaction, the bath temperature was reset to 40° C. At about 47 hours after the addition of the hexagonal boron nitride to the reaction, the bath temperature remained at 40° C., but the reaction temperature was about 48.5° C. A sample was removed, and test results showed a particle size of 1374.6 nm (Int. wt. avg.). At about 117 hours after the addition of the hexagonal boron nitride to the reaction, the bath temperature reached 58.1° C. and the reaction temperature was about 93° C. The load on the motor increased substantially. A sample was removed, and test results showed a particle size of 462.8 nm (Int. wt. avg.). Beginning at about 117.5 hours after the addition of the hexagonal boron nitride to the reaction, another 85.9 g of superphosphoric acid 105% was added to the reaction over about 45 minutes. Between about 144 and 162 hours after the addition of the hexagonal boron nitride to the reaction, the load on the motor increased and mixing was stopped. The bath temperature was reset to 80° C. At that temperature, an additional 22 g of superphosphoric acid 105% was added to the reaction mixture and mixing was carefully restarted. Following this, about 62.2 g of maleic anhydride was weighed up and mixed into the reaction. At about 163 hours following the addition of the hexagonal boron nitride to the reaction, the reaction was again mixing well with the bath temperature at 80° C., and the reaction temperature at about 95° C. At about 164 hours following the addition of the hexagonal boron nitride to the reaction, the temperature in the reactor had reached about 104° C. measured with an IR thermometer. At that point, the reaction was quenched dry by mixing into the reaction mixture 537.4 g of ammonium carbonate.

Run 2.

A reactor comprising a jacketed double arm sigma mixer is heated. A 125 g portion of 50% glyoxylic acid solution in water was added to the reactor. The jacket was heated with a heating bath set to about 40° C. A 125 g portion of β-cyclodextrin was added to the mixing glyoxylic acid solution in parts and allowed to mix to form a gel over about 2 minutes. Following formation of the gel, a 125 g portion of hexagonal boron nitride (325 mesh, Alfa Aesar) was added with mixing over about 3 to 7 minutes. After about 40 minutes following the first addition of guest particles (hexagonal boron nitride) into the reactor, the sides of the reactor were scraped to displace adhering material back into the reaction mixture. Thereafter, mixing improved and a lid was placed on the mixer. About an hour and 23 minutes following the first addition of hexagonal boron nitride into the reactor, the reaction mixture was observed to be sticking to the sides of the reactor and piling above the blades again. As a result, the temperature setpoint for the bath was raised to about 50° C. At about 2 hours and 30 minutes following the first addition of hexagonal boron nitride into the reactor, with the bath temperature at 50° C., the reaction was mixing well. Over the next 72 hours, the bath temperature was adjusted occasionally between about 30° C. and 50° C. to maintain mixing of the reaction mixture while also keeping the viscosity and the tackiness of the mixture elevated. At about 72 hours, a 19.4 g portion of superphosphoric acid 105% was added to the reaction with mixing.

At about 120 hours, an additional 20 g of superphosphoric acid 105% was added with mixing, and following this, at about 121.5 hours, 30.1 g of glucosamine sulfate was mixed into the reaction. The load on the mixture was observed to increase. At about 126 hours, the temperature of the reaction mixture was about 56° C. by IR thermometer without any heating from the bath. The reaction mixture continued to mix well. At about 167 hours, the temperature of the reaction mixture was about 65° C. by IR thermometer without any heating from the bath. At about 170 hours, a small sample was removed and dispersed in DI water with ammonia. The particle size was measured at 744 nm intensity weighted average. A portion of a dispersed sample was filtered through a 0.45 micron syringe filter, and this sample was tested for particle size. The filtered sample tested at about 145 nm intensity weighted average particle size. At about 174.5 hours, the load on the motor had become high, and the reaction mixture was about 90° C. by IR thermometer without any heating from the bath. The reaction mixture was also becoming darker. An additional 20 g of superphosphoric acid 105% was added with mixing and following this (at about 175 hours) another 20 g of superphosphoric acid 105% was added with mixing. At about 175.5 hours, the load on the motor remained high and another 41.3 g of superphosphoric acid 105% was added with mixing. The load on the motor decreased. At about 190 hours, the reaction temperature was about 73° C. by IR thermometer without any heating from the bath. A small sample was removed and dispersed in DI water with ammonia, and the particle size was measured at 792 nm intensity weighted average. At about 192.7 hours, 60 g of maleic anhydride was mixed into the reaction. At about 193 hours, a small sample was removed and dispersed in DI water with ammonia. The particle size was measured at 610 nm intensity weighted average. At about 198 hours, the reaction was dry quenched by mixing with about 266.7 g of ammonium carbonate.

Example 31: Dry Quenched Gel and Clathrate of the Inorganic Ceramic Material Hexagonal Boron Nitride A small portion of the dry quenched product of Example 30, Run 2, was dispersed in DI water with added ammonia 8 days after the reaction was dry-quenched. The particle size of this colloidal was measured (as described above) at 468.5 nm intensity weighted average. A portion of this dispersion was then filtered through a 0.45 micron pore size syringe filter, and the filtrate tested again for particle size. The particle size measured 198.1 nm intensity weighted average showing that the colloidal dispersion of the nanostructured boron nitride was stable to filtration.

Example 32: Gel and Clathrate Formation and Particle Size Reduction of Nanostructured Composite Particles of Pigment Red 122 with Shellac A gel was formed in accordance with the process of Example 10, with the bath temperature set at 60° C. and using about 16 units of superphosphoric acid and about 8 units of β-cyclodextrin. About 16 units of Pigment Red 122 was dry-blended with about 4.2 units of blonde shellac flakes. This dry blend of pigment and shellac was carefully added to the reactor allowing it to mix into the reaction mixture, in four approximately equal parts at intervals over about 1 hour. At about 1 hour and 16 minutes after the first pigment/shellac addition to the reactor, 4 units of glucono-lactone was added to the reaction with mixing. At about 5 hours and 20 minutes after the first pigment/shellac addition to the reactor, the temperature in the reactor was measured at about 75° C. with an IR thermometer. A sample was removed and tested for particle size. The particle size measured about 218.2 nm intensity weighted average. About 21 hours after the first pigment/shellac addition to the reactor, the reactor was opened, and the reaction mixture was noted to be adhering to the sides of the reactor above the mixing blades. At that time, the sides of the reactor were scraped to resume mixing of the reaction mixture and 4 parts of maleic anhydride were added into the reactor with mixing. About 2 hours following the addition of the maleic anhydride to the reactor, the reaction mixture was mixing well, and the temperature of the mixture was measured at 76° C. with an IR thermometer. About 4 hours following the addition of the maleic anhydride to the reactor, a small sample of the reaction mixture was removed and tested for particle size. The particle size measured at 165.9 nm intensity weighted average. About 26 hours following the addition of the maleic anhydride to the reactor, the reaction mixture was still mixing well. A small sample was removed and tested for particle size. The particle size measured 149.6 nm intensity weighted average. At that time, the reaction was dry quenched by mixing with about 250 g of ammonium carbonate until the powdery product could be collected from the reactor.

Example 33: Colloidal Dispersion of Nanostructured Composite Particles of Pigment Red 122 with Shellac About 200 g of the powder product from Example 32 was dispersed in about 2000 ml of DI water, and the pH of the dispersion was measured at about 6.8. This dispersion was ultra-filtered to purify and remove salts, and the lost volume of the permeate was made up with the addition of DI water. This diafiltration was continued until the conductivity of the permeate was below about 0.01 mS (milli Siemens) indicating salt removal. The de-salted dispersion was then filtered first through filter cloth and then through a nominal 1.5 micron glass fiber filter on a Buchner funnel. The particle size of this filtrate tested at about 183 nm intensity weighted average which dropped to about 155 nm with the addition of ammonium hydroxide. This dispersion was tested, and results revealed about 10% pigment solids by UV/visible spectroscopy.

Example 34: Inkjet Inks for Colloidal Dispersions Prepared from Nanostructured Particles Made by the Process Three formulations of ink, set forth as Run 1, Run 2 and Run 3 below, were used in the example. Colloidal dispersions of Pigment Red 122, Pigment Blue 15:4, and Pigment Yellow 180, prepared according to the invention, were each incorporated into the each of the three formulations below for a total of nine inks—each formulation comprising one of the pigment dispersions.

Run 1 Piezo Ink:

| | |
|---|---|
| BIT Biocide | 0.21% |
| Amine Buffer | 0.52% |
| Glycol Humectant A | 10.4% |
| Glycol Humectant B | 18.08% |
| Humectant C | 5.2% |
| Dispersion to give | 2% to 7% Pigment |
| Surfactant A | 0.1%-0.3% |
| Surfactant B | 0.1%-0.3% |
| Deionized Water | Balance |

Run 2 Piezo Ink:

| | |
|---|---|
| BIT Biocide | 0.1% |
| Amine Buffer A | 0.4% |
| Glycol Humectant A | 12% |
| Glycol Humectant B | 6% |
| Humectant C | 4% |
| Glycol Ether A | 3% |
| Dispersion to give | 2% to 7% Pigment |
| Surfactant A | 0.1%-0.3% |
| Surfactant B | 0.1%-0.3% |
| Deionized Water | Balance |

Run 3 Thermal Ink:

| | |
|---|---|
| BIT Biocide | 0.2% |
| Amine Buffer B | 0.8% |
| Glycol Humectant A | 10% |
| Glycol Ether B | 10% |
| Lower Alcohol | 3% |
| Dispersion to give | 2% to 7% Pigment |
| Surfactant A | 0.1%-0.3% |
| Surfactant B | 0.1%-0.3% |
| Deionized Water | Balance |

The inks were evaluated using both piezo and thermal inkjet printheads. All inks printed well using both printheads.

Example 35: Ink Prepared with Colloidal Dispersion of Nanostructured Composite Particles of Pigment Red 122 with Shellac The dispersion of Example 33 was used to prepare a Piezo ink according to the Piezo Ink formulation (Run 2) of Example 34. The ink was jetted onto corona treated polypropylene plastic films using an Epson Stylus C88+ Printer. These films were then stored at approximately 60° C. for about 12 to 16 hours. Following storage, it was found that prints prepared using the ink, without binder but with composite particles of pigment and shellac (Ex. 33), gave superior resistance to scratching and to peeling following removal of adhesive tape. (Results not shown).

Example 36: Inkjet Inks Formulated with Dihydrazide Crosslinkers for Colloidal Dispersions Prepared from Nanostructured Particles Made by the Process Inks formulated according to above Example 34, Run 2 formulation, were prepared using colloidal dispersions of Pigment Red (PR) 122, Pigment Blue (PB) 15:4 or Pigment Yellow (PY) 180. Three inks (one each of PR 122, PB 15:4, and PY 180) were modified with the addition of about 1.5% adipic acid dihydrazide. Adipic acid dihydrazide is a carbonyl reactive crosslinker able to react with carbonyl groups on the surface of the nanostructured particles and bridge their attachment to other carbonyl group containing molecules. Another three inks (one each of PR 122, PB 15:4 and PY 180) were modified with the addition of 1.5% adipic acid dihydrazide together with maltodextrin. Maltodextrin is a polysaccharide with an aldehyde group available to react with the other end of the adipic acid dihydrazide, thus allowing preparation of inks containing nanostructured particles with attached maltodextrin molecules at their surface. All of the inks showed good jetting and improved fastness properties.

In accordance with the patent statutes, the best mode and preferred embodiments have been set forth, the scope of the invention is not limited thereto, but rather by the scope of the attached claims.

What is claimed is:

1. A process for forming a nanoparticle, comprising:
   a. heating an acid medium with agitation;
   b. adding a host vessel comprising a carbohydrate with agitation to the acid medium to form a gel, wherein the carbohydrate is a simple sugar, a disaccharide, a polysaccharide or cyclodextrin;
   c. adding a solid guest particle with agitation to the gel to form a mixture;
   d. stirring the mixture at an elevated temperature for a set time to allow particle size reduction and annealing to occur;
   e. quenching the mixture with water or a dry basic compound;
   f. dispersing the quenched mixture in water to form a colloidal dispersion of nanoparticles;
   g. filtering the colloidal dispersion; and
   h. stabilizing the filtered colloidal dispersion of nanoparticles by (i) carboxymethylation of the nanoparticles using an acid, wherein the acid is chloroacetic acid or dichloroacetic acid or (ii) by reacting the dispersion with another reactive component that is a base comprising a sodium or other alkali metal hydroxide.

2. The process of claim 1, wherein the disaccharide is sucrose and the cyclodextrin is β-cyclodextrin.

3. The process of claim 1, further comprising:
   improving the chroma or shade of the nanoparticles by reacting the filtered colloidal dispersion with hydrogen peroxide, sodium percarbonate, or other peroxide bond containing compound.

4. The process of claim 3, further comprising:
   changing the affinity of the nanoparticles for a surface by reacting the nanoparticles with a dihydrazide, wherein the dihydrazide is adipic acid dihydrazide.

5. The process of claim 1, wherein a cyclic anhydride, a dieneophile, a conjugate addition acceptor compound, a lactone, or a lactam compound is added at the time of particle size reduction and annealing stage and prior to the quenching stage as a processing aid and to improve the stability of a colloidal dispersion prepared from the resulting nanoparticles.

6. The process of claim 5, wherein the cyclic anhydride is maleic anhydride or glutaric anhydride; wherein the dienophile is maleic anhydride; wherein the conjugate addition acceptor compound is maleic anhydride; and wherein the lactone is carbohydrate-derived lactone.

7. The process of claim 6, wherein the carbohydrate-derived lactone is gluconolactone.

8. The process of claim 1, wherein a processing aid is added at the particle size reduction and annealing stage and prior to the quenching stage, to improve the adhesive properties of the resulting nanoparticles and to improve the properties of a colloidal dispersion of the nanoparticles.

9. The process of claim 8, wherein the processing aid is a thermoplastic component.

10. The process of claim 9, wherein the thermoplastic component is shellac.

11. The process of claim 1, wherein the dry, basic compound for quenching is sodium carbonate or ammonium carbonate.

12. A process for preparing a stable, colloidal dispersion of boron nitride nanoparticles, comprising:
   a. heating an acid medium in a reactor with mixing, wherein the acid medium is a 50% glyoxylic acid solution;
   b. adding a host vessel comprising β-cyclodextrin with mixing to the acid medium to form a gel;
   c. adding a solid guest particle that is hexagonal boron nitride to the gel with mixing to the gel to form a reaction mixture;
   d. stirring the reaction mixture at elevated temperatures over time to allow particle size reduction and annealing to occur;
   e. adding an additional acid that is superphosphoric acid 105% to the reaction mixture at least once during the particle size reduction and annealing stage, with mixing;
   f. adding glucosamine to the reaction mixture with mixing;
   g. optionally, adding maleic anhydride to the reaction mixture with mixing; and
   h. dry quenching the mixture with a dry basic compound, wherein the temperatures for the reaction range between 30° C. and 110° C. and are adjusted with the range to maintain mixing or the reaction mixture and to keep viscosity and tackiness of the reaction mixture elevated.

* * * * *